United States Patent
Shafer et al.

(10) Patent No.: US 8,646,921 B2
(45) Date of Patent: Feb. 11, 2014

(54) REFLECTIVE MARKER BEING RADIO-OPAQUE FOR MRI

(75) Inventors: Helen Zinreich Shafer, Owings Mills, MD (US); David Alan Zinreich, Owings Mills, MD (US); Douglas Crumb, Owings Mills, MD (US)

(73) Assignee: IZI Medical Products, Owings Mills, MD (US)

( * ) Notice: Subject to any disclaimer, the term of this patent is extended or adjusted under 35 U.S.C. 154(b) by 136 days.

(21) Appl. No.: 13/408,386

(22) Filed: Feb. 29, 2012

(65) Prior Publication Data
US 2013/0135735 A1 May 30, 2013

Related U.S. Application Data

(60) Provisional application No. 61/565,099, filed on Nov. 30, 2011.

(51) Int. Cl.
*G02B 5/132* (2006.01)

(52) U.S. Cl.
USPC .......................................................... 359/544

(58) Field of Classification Search
USPC .................................. 359/515, 536, 543–545
See application file for complete search history.

(56) References Cited

U.S. PATENT DOCUMENTS

| | | |
|---|---|---|
| 3,203,289 A | 8/1965 | Beekley |
| 3,354,467 A | 11/1967 | Beekley |
| 3,941,127 A | 3/1976 | Froning |
| 4,126,126 A | 11/1978 | Bare et al. |
| D255,148 S | 5/1980 | Robinson et al. |
| 4,202,349 A | 5/1980 | Jones |
| 4,292,977 A | 10/1981 | Krause et al. |
| 4,326,534 A | 4/1982 | Axelgaard et al. |
| 4,365,634 A | 12/1982 | Bare et al. |
| 4,372,321 A | 2/1983 | Robinson |
| 4,377,869 A | 3/1983 | Venalainen et al. |
| 4,392,236 A | 7/1983 | Sandstrom et al. |
| 4,393,584 A | 7/1983 | Bare et al. |
| 4,401,356 A | 8/1983 | Bare |
| 4,416,286 A | 11/1983 | Iinuma et al. |
| 4,522,211 A | 6/1985 | Bare et al. |
| 4,676,776 A | 6/1987 | Howson |
| 4,702,256 A | 10/1987 | Robinson et al. |

(Continued)

FOREIGN PATENT DOCUMENTS

| | | |
|---|---|---|
| EP | 0941488 A1 | 9/1999 |
| EP | 0890117 B1 | 1/2002 |

(Continued)

*Primary Examiner* — Euncha Cherry
(74) *Attorney, Agent, or Firm* — Alchemy-Partners, PC; Ajay A. Jagtiani

(57) ABSTRACT

Described is a device comprising a retro-reflective marker sphere comprising: a core ball comprising: a generally spherical body portion, a mounting base extending from one end of the body portion of the core ball, and a mounting recess having a recess opening in the mounting base and extending into the body portion of the core ball, and a retro-reflective covering on the core ball, the retro-reflective covering comprising an opening through which the mounting base of the core ball extends, wherein a flat lower surface of the mounting base is spaced proximally from a lower edge of the opening of the retro-reflective covering, and wherein the mounting recess includes an interior screw thread for engaging an exterior screw thread of a mounting post when the retro-reflective marker sphere is mounted on the mounting post.

8 Claims, 22 Drawing Sheets

(56) References Cited

U.S. PATENT DOCUMENTS

| | | |
|---|---|---|
| 4,722,733 A | 2/1988 | Howson |
| 4,733,661 A | 3/1988 | Palestrant |
| 4,734,674 A | 3/1988 | Thomas et al. |
| 4,795,437 A | 1/1989 | Schulte et al. |
| 4,804,054 A | 2/1989 | Howson et al. |
| 4,810,243 A | 3/1989 | Howson |
| 4,846,797 A | 7/1989 | Howson et al. |
| 4,880,971 A | 11/1989 | Danisch |
| 4,908,017 A | 3/1990 | Howson et al. |
| 4,938,233 A | 7/1990 | Orrison, Jr. |
| 4,950,255 A | 8/1990 | Brown et al. |
| 4,964,855 A | 10/1990 | Todd et al. |
| 4,981,142 A | 1/1991 | Dachman |
| 5,054,480 A | 10/1991 | Bare et al. |
| 5,056,523 A | 10/1991 | Hotchkiss, Jr. et al. |
| 5,088,981 A | 2/1992 | Howson et al. |
| 5,103,997 A | 4/1992 | Shillington et al. |
| 5,184,720 A | 2/1993 | Packer et al. |
| 5,197,476 A | 3/1993 | Nowacki et al. |
| 5,198,877 A | 3/1993 | Schulz |
| 5,232,452 A | 8/1993 | Russell et al. |
| 5,249,581 A | 10/1993 | Horbal et al. |
| 5,290,248 A | 3/1994 | Bierman et al. |
| 5,295,483 A | 3/1994 | Nowacki et al. |
| 5,306,271 A | 4/1994 | Zinreich et al. |
| 5,314,411 A | 5/1994 | Bierman et al. |
| 5,321,257 A | 6/1994 | Danisch |
| 5,365,952 A | 11/1994 | Noble et al. |
| 5,368,030 A | 11/1994 | Zinreich et al. |
| 5,383,234 A | 1/1995 | Russell |
| 5,407,440 A | 4/1995 | Zinreich et al. |
| 5,427,099 A | 6/1995 | Adams |
| 5,435,066 A | 7/1995 | Bare et al. |
| 5,469,847 A | 11/1995 | Zinreich et al. |
| 5,474,569 A | 12/1995 | Zinreich et al. |
| 5,475,451 A | 12/1995 | Robert et al. |
| 5,523,581 A | 6/1996 | Cadwalader |
| 5,545,993 A | 8/1996 | Taguchi et al. |
| 5,577,995 A | 11/1996 | Walker et al. |
| 5,609,827 A | 3/1997 | Russell et al. |
| 5,628,733 A | 5/1997 | Zinreich et al. |
| 5,633,494 A | 5/1997 | Danisch |
| 5,665,653 A | 9/1997 | Bare et al. |
| 5,702,128 A | 12/1997 | Maxim et al. |
| 5,714,105 A | 2/1998 | Gysin et al. |
| 5,743,899 A | 4/1998 | Zinreich |
| RE35,816 E | 6/1998 | Schulz |
| 5,772,642 A | 6/1998 | Ciamacco, Jr. et al. |
| 5,795,335 A | 8/1998 | Zinreich |
| 5,806,515 A | 9/1998 | Bare et al. |
| 5,817,105 A | 10/1998 | Van Der Brug |
| 5,827,202 A | 10/1998 | Miraki et al. |
| 5,828,770 A | 10/1998 | Leis et al. |
| 5,833,682 A | 11/1998 | Amplatz et al. |
| 5,841,830 A | 11/1998 | Barni et al. |
| 5,848,125 A | 12/1998 | Arnett |
| 5,887,437 A | 3/1999 | Maxim |
| 5,908,410 A | 6/1999 | Weber et al. |
| 5,923,417 A | 7/1999 | Leis |
| 5,947,950 A | 9/1999 | Shillington et al. |
| 5,954,648 A | 9/1999 | Van Der Brug |
| 5,967,982 A | 10/1999 | Barnett |
| 5,989,182 A | 11/1999 | Hori et al. |
| RE36,461 E | 12/1999 | Russell et al. |
| 6,013,087 A | 1/2000 | Adams et al. |
| 6,024,216 A | 2/2000 | Shillington et al. |
| 6,041,094 A | 3/2000 | Russell |
| 6,045,565 A | 4/2000 | Ellis et al. |
| D424,530 S | 5/2000 | Kurtz et al. |
| 6,059,718 A | 5/2000 | Taniguchi et al. |
| 6,061,644 A | 5/2000 | Leis |
| 6,127,672 A | 10/2000 | Danisch |
| 6,179,860 B1 | 1/2001 | Fulton, III et al. |
| 6,264,599 B1 | 7/2001 | Slater et al. |
| 6,268,605 B1 | 7/2001 | Orava et al. |
| 6,269,148 B1 | 7/2001 | Jessop et al. |
| D447,567 S | 9/2001 | Murphy et al. |
| 6,288,785 B1 | 9/2001 | Frantz et al. |
| 6,300,138 B1 | 10/2001 | Gleason et al. |
| 6,302,870 B1 | 10/2001 | Jacobsen et al. |
| 6,379,319 B1 | 4/2002 | Garibotto et al. |
| 6,385,482 B1 | 5/2002 | Boksberger et al. |
| 6,422,048 B1 | 7/2002 | Fontes et al. |
| 6,485,465 B2 | 11/2002 | Moberg et al. |
| 6,490,473 B1 | 12/2002 | Katznelson et al. |
| 6,494,835 B1 | 12/2002 | Ciezki et al. |
| 6,537,205 B1 | 3/2003 | Smith |
| 6,553,326 B1 | 4/2003 | Kirsch et al. |
| 6,554,848 B2 | 4/2003 | Boylan et al. |
| 6,582,417 B1 | 6/2003 | Ledesma et al. |
| 6,625,563 B2 | 9/2003 | Kirsch et al. |
| 6,626,445 B2 | 9/2003 | Murphy et al. |
| 6,659,980 B2 | 12/2003 | Moberg et al. |
| 6,676,610 B2 | 1/2004 | Morton et al. |
| 6,685,644 B2 | 2/2004 | Seo et al. |
| 6,685,666 B1 | 2/2004 | Fontenot |
| 6,689,142 B1 | 2/2004 | Tremaglio, Jr. et al. |
| 6,712,785 B2 | 3/2004 | Morton et al. |
| 6,714,628 B2 | 3/2004 | Broyles et al. |
| 6,782,289 B1 | 8/2004 | Strauss |
| 6,826,257 B2 | 11/2004 | Sayre et al. |
| 6,836,745 B2 | 12/2004 | Seiler et al. |
| 6,845,271 B2 | 1/2005 | Fang et al. |
| D503,980 S | 4/2005 | Sayre et al. |
| 6,875,184 B2 | 4/2005 | Morton et al. |
| 6,899,696 B2 | 5/2005 | Morton et al. |
| 6,903,307 B1 | 6/2005 | McConnell et al. |
| 6,907,293 B2 | 6/2005 | Grill et al. |
| D510,169 S | 9/2005 | Deane et al. |
| 6,981,950 B2 | 1/2006 | Morton et al. |
| 6,985,558 B1 | 1/2006 | Russell |
| 6,990,427 B2 | 1/2006 | Kirsch et al. |
| 7,047,078 B2 | 5/2006 | Boggs, II et al. |
| 7,066,985 B2 | 6/2006 | Deane et al. |
| D528,212 S | 9/2006 | Conway et al. |
| 7,120,499 B2 | 10/2006 | Thrope et al. |
| 7,127,040 B2 | 10/2006 | Sayre et al. |
| 7,135,059 B2 | 11/2006 | Deane et al. |
| 7,137,712 B2 | 11/2006 | Brunner et al. |
| 7,140,769 B2 | 11/2006 | Kay |
| 7,194,296 B2 | 3/2007 | Frantz et al. |
| D539,530 S | 4/2007 | Sanderson et al. |
| 7,204,796 B1 | 4/2007 | Seiler |
| 7,206,626 B2 | 4/2007 | Quaid, III |
| D545,660 S | 7/2007 | Robinson et al. |
| D547,048 S | 7/2007 | Conway et al. |
| 7,239,918 B2 | 7/2007 | Strother et al. |
| 7,245,958 B1 | 7/2007 | Navab et al. |
| 7,263,159 B2 | 8/2007 | Russell |
| D552,735 S | 10/2007 | Archambault |
| 7,283,867 B2 | 10/2007 | Strother et al. |
| D559,985 S | 1/2008 | Dzierlatka |
| D559,987 S | 1/2008 | Strother et al. |
| 7,341,841 B2 | 3/2008 | Metzger et al. |
| 7,343,202 B2 | 3/2008 | Mrva et al. |
| 7,346,417 B2 | 3/2008 | Luth et al. |
| 7,353,125 B2 | 4/2008 | Nieminen et al. |
| 7,364,553 B2 | 4/2008 | Paz et al. |
| 7,376,467 B2 | 5/2008 | Thrope et al. |
| 7,438,745 B2 | 10/2008 | Deane et al. |
| D581,530 S | 11/2008 | Thierfelder et al. |
| 7,457,443 B2 | 11/2008 | Persky |
| 7,465,847 B2 | 12/2008 | Fabian |
| 7,468,043 B2 | 12/2008 | Morton et al. |
| 7,469,187 B2 | 12/2008 | Nieminen et al. |
| 7,491,198 B2 | 2/2009 | Kockro |
| 7,496,222 B2 | 2/2009 | Mussack et al. |
| D590,948 S | 4/2009 | Archambault |
| D590,949 S | 4/2009 | Broyles |
| 7,529,387 B2 | 5/2009 | Kotake et al. |
| 7,549,960 B2 | 6/2009 | Govari |
| 7,565,198 B2 | 7/2009 | Bennett et al. |
| 7,571,000 B2 | 8/2009 | Boggs, II et al. |
| 7,571,002 B2 | 8/2009 | Thrope et al. |

(56) References Cited

U.S. PATENT DOCUMENTS

| | | | |
|---|---|---|---|
| 7,575,557 B2 | 8/2009 | Morton et al. |
| 7,577,474 B2 | 8/2009 | Vilsmeier |
| D602,590 S | 10/2009 | Dzierlatka |
| 7,617,932 B2 | 11/2009 | Windus-Smith et al. |
| 7,623,925 B2 | 11/2009 | Grill et al. |
| 7,627,137 B2 | 12/2009 | Takemoto |
| 7,637,913 B2 | 12/2009 | De Villiers et al. |
| 7,651,506 B2 | 1/2010 | Bova et al. |
| D609,255 S | 2/2010 | Bare et al. |
| D610,261 S | 2/2010 | Strother et al. |
| 7,687,239 B2 | 3/2010 | Goldberg et al. |
| 7,696,876 B2 | 4/2010 | Dimmer et al. |
| 7,696,899 B2 | 4/2010 | Immerz et al. |
| 7,706,600 B2 | 4/2010 | Kreeger et al. |
| 7,729,475 B2 | 6/2010 | Kito et al. |
| 7,730,887 B2 | 6/2010 | Deane et al. |
| D619,728 S | 7/2010 | Bare et al. |
| 7,758,541 B2 | 7/2010 | Wallace et al. |
| 7,760,909 B2 | 7/2010 | Manus |
| 7,761,167 B2 | 7/2010 | Bennett et al. |
| 7,763,030 B2 | 7/2010 | Blau et al. |
| 7,771,339 B2 | 8/2010 | Isacsson et al. |
| 7,781,041 B2 | 8/2010 | Broyles |
| 7,783,441 B2 | 8/2010 | Nieminen et al. |
| 7,794,469 B2 | 9/2010 | Kao et al. |
| 7,797,058 B2 | 9/2010 | Mrva et al. |
| D625,345 S | 10/2010 | Bare et al. |
| D625,428 S | 10/2010 | Bare et al. |
| 7,806,858 B2 | 10/2010 | Smith et al. |
| 7,809,184 B2 | 10/2010 | Neubauer et al. |
| 7,813,809 B2 | 10/2010 | Strother et al. |
| 7,820,446 B2 | 10/2010 | Feikas et al. |
| D627,469 S | 11/2010 | Dzierlatka |
| D631,547 S | 1/2011 | Sayre et al. |
| 7,865,236 B2 | 1/2011 | Cory et al. |
| 7,865,250 B2 | 1/2011 | Mrva et al. |
| 7,874,686 B2 | 1/2011 | Rossner et al. |
| 7,878,981 B2 | 2/2011 | Strother et al. |
| 7,883,545 B2 | 2/2011 | Tuma |
| 7,894,913 B2 | 2/2011 | Boggs et al. |
| 7,896,815 B2 | 3/2011 | Thrope et al. |
| 7,922,391 B2 | 4/2011 | Essenreiter et al. |
| 7,922,731 B2 | 4/2011 | Schumacher et al. |
| 7,945,311 B2 | 5/2011 | McCloy et al. |
| 7,957,925 B2 | 6/2011 | Nieminen et al. |
| 7,962,189 B2 | 6/2011 | Numada et al. |
| 7,972,300 B2 | 7/2011 | Smith et al. |
| 7,983,739 B2 | 7/2011 | Dunki-Jacobs et al. |
| D643,928 S | 8/2011 | Dzierlatka |
| 7,996,092 B2 | 8/2011 | Mrva et al. |
| 8,012,295 B1 | 9/2011 | Broyles |
| 8,023,712 B2 | 9/2011 | Ikuma et al. |
| 8,051,856 B2 | 11/2011 | Bare et al. |
| 8,052,649 B2 | 11/2011 | Wright |
| 8,071,319 B2 | 12/2011 | Metzger et al. |
| 8,083,759 B2 | 12/2011 | Cox et al. |
| 8,088,104 B2 | 1/2012 | Smith et al. |
| 8,090,428 B2 | 1/2012 | De Villiers et al. |
| 8,104,958 B2 | 1/2012 | Weiser et al. |
| 8,126,530 B2 | 2/2012 | Bare et al. |
| 8,126,535 B2 | 2/2012 | Maier et al. |
| 8,128,576 B2 | 3/2012 | Tracey et al. |
| 2004/0243146 A1 | 12/2004 | Chesbrough et al. |
| 2005/0112758 A1 | 5/2005 | Archambault et al. |
| 2005/0228410 A1 | 10/2005 | Berreklouw |
| 2005/0261579 A1 | 11/2005 | Boehm, Jr. et al. |
| 2005/0284982 A1 | 12/2005 | Kasper |
| 2006/0063973 A1 | 3/2006 | Makower et al. |
| 2006/0149345 A1 | 7/2006 | Boggs, II et al. |
| 2006/0173356 A1 | 8/2006 | Feilkas |
| 2006/0200178 A1 | 9/2006 | Hamel et al. |
| 2006/0200219 A1 | 9/2006 | Thrope et al. |
| 2007/0060968 A1 | 3/2007 | Strother et al. |
| 2007/0060980 A1 | 3/2007 | Strother et al. |
| 2007/0066995 A1 | 3/2007 | Strother et al. |
| 2007/0093709 A1 | 4/2007 | Abernathie |
| 2007/0238983 A1 | 10/2007 | Suthanthiran et al. |
| 2007/0239224 A1 | 10/2007 | Bennett et al. |
| 2007/0255212 A1 | 11/2007 | Smith et al. |
| 2007/0270921 A1 | 11/2007 | Strother et al. |
| 2007/0293910 A1 | 12/2007 | Strother et al. |
| 2008/0033500 A1 | 2/2008 | Strother et al. |
| 2008/0039866 A1 | 2/2008 | Stetz et al. |
| 2008/0065171 A1 | 3/2008 | Fang et al. |
| 2008/0071322 A1 | 3/2008 | Mrva et al. |
| 2008/0091224 A1 | 4/2008 | Griffis, III et al. |
| 2008/0091266 A1 | 4/2008 | Griffis, III et al. |
| 2008/0107305 A1 | 5/2008 | Vanderkooy et al. |
| 2008/0132969 A1 | 6/2008 | Bennett et al. |
| 2008/0132974 A1 | 6/2008 | Strother et al. |
| 2008/0139916 A1 | 6/2008 | Maier et al. |
| 2008/0146942 A1 | 6/2008 | Dala-Krishna |
| 2008/0161874 A1 | 7/2008 | Bennett et al. |
| 2008/0172119 A1 | 7/2008 | Yamasaki et al. |
| 2008/0177351 A1 | 7/2008 | Fang et al. |
| 2008/0200844 A1 | 8/2008 | Millahn et al. |
| 2008/0249397 A1 | 10/2008 | Kapadia |
| 2008/0281989 A1 | 11/2008 | Hager et al. |
| 2008/0287782 A1 | 11/2008 | Traboulsi et al. |
| 2008/0306379 A1 | 12/2008 | Ikuma et al. |
| 2008/0312673 A1 | 12/2008 | Viswanathan et al. |
| 2009/0030380 A1 | 1/2009 | Binmoeller |
| 2009/0036775 A1 | 2/2009 | Ikuma et al. |
| 2009/0087380 A1 | 4/2009 | Fasching et al. |
| 2009/0132018 A1 | 5/2009 | DiUbaldi et al. |
| 2009/0171324 A1 | 7/2009 | Chong et al. |
| 2009/0216116 A1 | 8/2009 | Roger |
| 2009/0259126 A1 | 10/2009 | Saal et al. |
| 2009/0281421 A1 | 11/2009 | Culp et al. |
| 2009/0287467 A1 | 11/2009 | Sparks et al. |
| 2009/0289182 A1 | 11/2009 | Pavsner |
| 2009/0299416 A1 | 12/2009 | Hanni et al. |
| 2009/0305315 A1 | 12/2009 | Gandola et al. |
| 2010/0036445 A1 | 2/2010 | Sakai et al. |
| 2010/0036454 A1 | 2/2010 | Bennett et al. |
| 2010/0070069 A1 | 3/2010 | Hofstadler et al. |
| 2010/0075430 A1 | 3/2010 | Hofstadler et al. |
| 2010/0076455 A1 | 3/2010 | Birkenbach et al. |
| 2010/0100081 A1 | 4/2010 | Tuma et al. |
| 2010/0113860 A1 | 5/2010 | Traboulsi et al. |
| 2010/0113912 A1 | 5/2010 | Traboulsi et al. |
| 2010/0128558 A1 | 5/2010 | Hofstadler et al. |
| 2010/0136570 A1 | 6/2010 | Goldberg et al. |
| 2010/0137857 A1 | 6/2010 | Shroff et al. |
| 2010/0152808 A1 | 6/2010 | Boggs, II |
| 2010/0152809 A1 | 6/2010 | Boggs, II |
| 2010/0158869 A1 | 6/2010 | Kaemmerer |
| 2010/0191114 A1 | 7/2010 | Hyun et al. |
| 2010/0219336 A1 | 9/2010 | Hofstadler et al. |
| 2010/0268151 A1 | 10/2010 | Mauge et al. |
| 2010/0274310 A1 | 10/2010 | Boggs, II et al. |
| 2010/0312247 A1 | 12/2010 | Tuma |
| 2010/0324484 A1 | 12/2010 | Smith et al. |
| 2011/0014027 A1 | 1/2011 | Drader et al. |
| 2011/0029071 A1 | 2/2011 | Zlotnick et al. |
| 2011/0051892 A1 | 3/2011 | Shafer |
| 2011/0077628 A1 | 3/2011 | Hoey et al. |
| 2011/0086114 A1 | 4/2011 | Zinreich et al. |
| 2011/0093032 A1 | 4/2011 | Boggs, II et al. |
| 2011/0118627 A1 | 5/2011 | Morton et al. |
| 2011/0152600 A1 | 6/2011 | Scott et al. |
| 2011/0166417 A1 | 7/2011 | Lin |
| 2011/0224537 A1 | 9/2011 | Brunner |
| 2011/0230906 A1 | 9/2011 | Modesitt et al. |
| 2011/0286098 A1* | 11/2011 | Hauri et al. .......... 359/543 |

FOREIGN PATENT DOCUMENTS

| | | |
|---|---|---|
| EP | 1244394 B1 | 10/2002 |
| EP | 1251778 B1 | 10/2002 |
| EP | 1272862 B1 | 1/2003 |
| EP | 0847253 B1 | 3/2003 |
| EP | 1303771 B1 | 4/2003 |
| EP | 1330183 A2 | 7/2003 |

(56) References Cited

FOREIGN PATENT DOCUMENTS

| | | | |
|---|---|---|---|
| EP | 1034440 | B1 | 10/2003 |
| EP | 1158924 | B1 | 3/2004 |
| EP | 1399765 | B1 | 3/2004 |
| EP | 0836438 | B1 | 9/2004 |
| EP | 1535021 | A2 | 6/2005 |
| EP | 1613213 | A1 | 1/2006 |
| EP | 1698373 | B1 | 9/2006 |
| EP | 1720606 | B1 | 11/2006 |
| EP | 1096268 | B1 | 12/2006 |
| EP | 1761303 | A2 | 3/2007 |
| EP | 1786511 | A2 | 5/2007 |
| EP | 1865342 | A3 | 12/2007 |
| EP | 1761303 | A4 | 1/2008 |
| EP | 1885438 | A1 | 2/2008 |
| EP | 1993440 | A2 | 11/2008 |
| EP | 2024018 | A2 | 2/2009 |
| EP | 2092899 | A2 | 8/2009 |
| EP | 2106273 | A2 | 10/2009 |
| EP | 2024018 | A4 | 4/2010 |
| EP | 2269507 | A1 | 1/2011 |
| EP | 2052681 | A3 | 2/2011 |
| EP | 2318088 | A1 | 5/2011 |
| EP | 1786511 | A4 | 8/2011 |
| WO | WO 2006/002559 | A1 | 1/2006 |
| WO | WO 2010/127811 | A2 | 11/2010 |

* cited by examiner

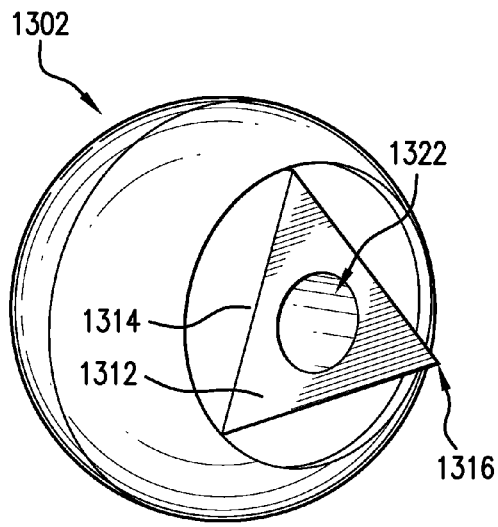
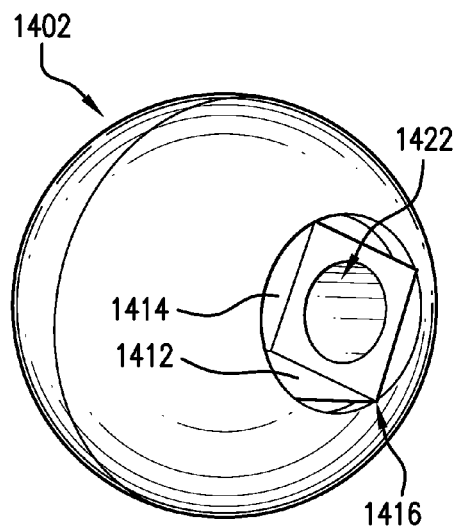
FIG.13  FIG.14
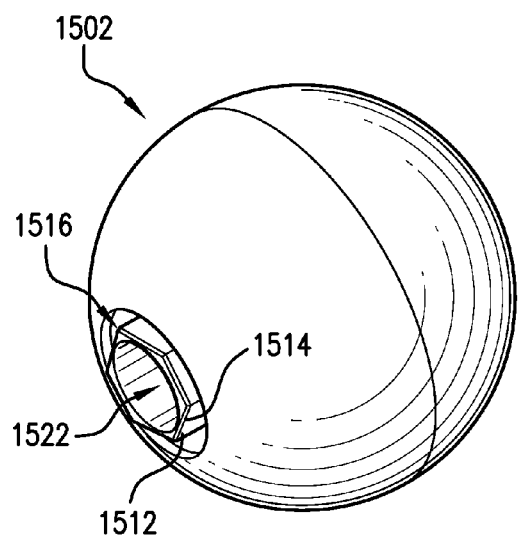
FIG.15

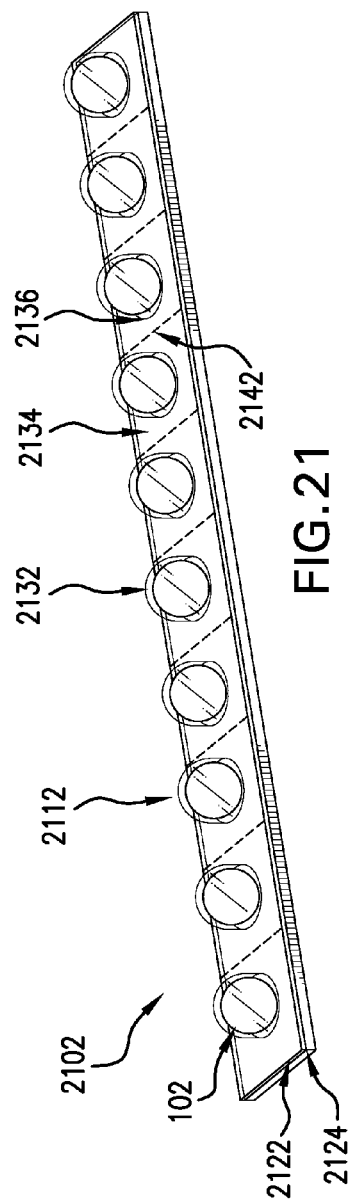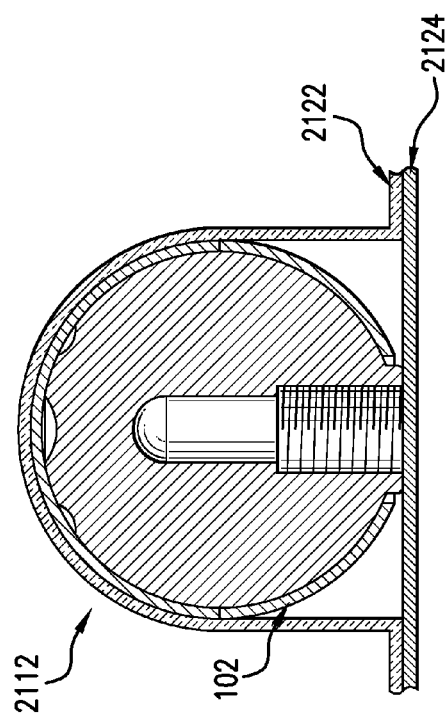

REFLECTIVE MARKER BEING RADIO-OPAQUE FOR MRI

CROSS-REFERENCE TO RELATED APPLICATIONS

This application claims benefit of priority to U.S. Provisional Patent Application No. 61/565,099 to Shafer, entitled NOVEL SNAP-ON-SPHERE, filed Nov. 30, 2011, which is incorporated herein by reference in its entirety. This application also claims priority to the following applications filed Feb. 29, 2011 to the same inventors as the present application: application Ser. No. 13/408,046 entitled "RADIOPAQUE CORE," application Ser. No. 13/408,126 entitled "RETRO-REFLECTIVE MARKER WITH SNAP ON THREADED POST," application Ser. No. 13/408,272 entitled "MATERIAL THICKNESS CONTROL OVER RETRO-REFLECTIVE MARKER," application Ser. No. 13/408,387 entitled "PACKAGING FOR RETRO-REFLECTIVE MARKERS," application Ser. No. 13/408,317 entitled "HIGH REFLECTIVITY RETRO-REFLECTIVE MARKER," application Ser. No. 13/408,124 entitled "RETRO-REFLECTIVE MARKER INCLUDING COLORED MOUNTING PORTION," application Ser. No. 13/408,070 entitled "MARKER SPHERE INCLUDING EDGED OPENING TO AID IN MOLDING," and application Ser. No. 13/408,035 entitled "REFLECTIVE MARKER WITH ALIGNMENT FEATURE," the entire content and disclosures of which are incorporated herein by reference in their entirety.

BACKGROUND

1. Field of the Invention

The present invention relates to retro-reflective markers for image-guided surgery.

2. Related Art

Systems for obtaining coordinates of a point or points of interest include marker-tracking systems. Such marker-tracking systems typically rely on objects having one or more markers affixed thereto. The markers that are affixed to the object may be active markers (e.g., light-emitting diode markers), passive markers (e.g., retro-reflective markers) or a combination of active and passive markers. In a medical application context, such as image-guided surgery, a user (e.g., a doctor) touches the surface of interest (e.g., a surface of a patient's body) using the distal tip of an object (e.g., a probe or a surgical instrument). A marker-sensing device (e.g., a pair of cameras) views the marker(s) affixed to the object. On the basis of the known locations of the cameras and the location(s) of the marker(s) as seen by each camera, such systems calculate the three-dimensional coordinates of the marker(s). Then, on the basis of the known relationship between the location(s) of the marker(s) and the location of the object tip, the marker-tracking system determines the coordinates of the object's tip. With the object's tip on the surface, those coordinates also correspond to the coordinates of the surface at that point.

SUMMARY

According to a first broad aspect, the present invention provides a device comprising a retro-reflective marker sphere comprising: a core ball comprising: a generally spherical body portion, and a mounting recess extending into the body portion of the core ball, and a retro-reflective covering on the core ball, wherein the retro-reflective covering has an opening aligned with the mounting recess of the core ball, wherein the mounting recess includes one or more interior engagement structures for engaging one or more exterior engagement structures of a mounting post when the retro-reflective marker sphere is mounted on the mounting post, and wherein the core ball is greater than 12% radiopaque.

According to a second broad aspect, the present invention provides a device comprising a retro-reflective marker sphere comprising: a core ball comprising: a generally spherical body portion, and a mounting recess extending into the body portion of the core ball, and a retro-reflective covering on the core ball, wherein the retro-reflective covering has an opening aligned with the mounting recess of the core ball, and wherein the mounting recess includes a semi-locking interior screw thread for engaging an exterior screw thread of a mounting post and for causing an audible snap when the retro-reflective marker sphere is snapped onto the mounting post.

According to a third broad aspect, the present invention provides a device comprising a retro-reflective marker sphere comprising: a core ball comprising: a generally spherical body portion, and a mounting recess extending into the body portion of the core ball, and a retro-reflective covering on the core ball, wherein the retro-reflective covering has an opening aligned with the mounting recess of the core ball, wherein the mounting recess includes one or more interior engagement structures for engaging one or more exterior engagement structures of a mounting post when the retro-reflective marker sphere is mounted on a mounting post, and wherein the thickness of the retro-reflective covering varies by no more than 0.00762 cm.

According to a fourth broad aspect, the present invention provides a device comprising a retro-reflective marker sphere comprising: a core ball comprising: a generally spherical body portion, and a mounting recess extending into the body portion of the core ball, and a retro-reflective covering on the core ball, wherein the retro-reflective covering has an opening aligned with the mounting recess of the core ball, wherein the mounting recess includes one or more interior engagement structures for engaging one or more exterior engagement structures of a mounting post when the retro-reflective marker sphere is mounted on a mounting post, and wherein the core ball comprises an MRI filling material contained in the core ball.

According to a fifth broad aspect, the present invention provides a package comprising: a pocket layer including one or more pockets for receiving one or more retro-reflective marker spheres, and one or more backing layers joined to the pocket layer, wherein at least one of the one or more backing layers includes a recess for receiving a polygonal mounting base of a retro-reflective marker sphere of the one or more retro-reflective marker spheres to thereby maintain the retro-reflective marker sphere in a right-side-up orientation.

According to a sixth broad aspect, the present invention provides a package comprising: a pocket layer including one or more pockets for receiving one or more respective retro-reflective marker spheres, and one or more backing layers joined to the pocket layer, wherein at least one of the one or more backing layers includes a mounting base opening for receiving a mounting base of a retro-reflective marker sphere of the one or more retro-reflective marker sphere so that the mounting base extends through the mounting base opening to thereby maintain the retro-reflective marker sphere in a right-side-up orientation.

According to a seventh broad aspect, the present invention provides a package comprising: a pocket layer including one or more pockets for receiving one or more retro-reflective marker spheres, one or more backing layers joined to the pocket layer by an adhesive, and a retro-reflective marker sphere contained in the package, wherein the adhesive has a peel strength of no greater than 22.24 N of force.

According to an eighth broad aspect, the present invention provides a package comprising: a pocket layer including one or more pockets for receiving one or more retro-reflective marker spheres, one or more backing layers joined to the pocket layer, wherein at least one of the one or more backing layers comprises a rupturable material joined to the pocket layer, and a retro-reflective marker sphere contained in the package.

According to a ninth broad aspect, the present invention provides a device comprising a retro-reflective marker sphere comprising: a core ball comprising: a generally spherical body portion, and a mounting recess extending into the body portion of the core ball, and a retro-reflective covering on the core ball, wherein the retro-reflective covering has an opening aligned with the mounting recess of the core ball, wherein the mounting recess includes one or more interior engagement structures for engaging one or more exterior engagement structures of a mounting post when the retro-reflective marker sphere is mounted on a mounting post, and wherein the retro-reflective covering is gold-colored.

According to a tenth broad aspect, the present invention provides a device comprising a retro-reflective marker sphere comprising: a core ball comprising: a generally spherical body portion, and a mounting recess extending into the body portion of the core ball, and a retro-reflective covering on the core ball, wherein the retro-reflective covering has an opening aligned with the mounting recess of the core ball, wherein the mounting recess includes one or more interior engagement structures for engaging one or more exterior engagement structures of a mounting post when the retro-reflective marker sphere is mounted on a mounting post, and wherein the retro-reflective covering is chrome-colored.

According to an eleventh broad aspect, the present invention provides a device comprising a retro-reflective marker sphere comprising: a core ball comprising: a generally spherical body portion, and a mounting recess extending into the body portion of the core ball, and a retro-reflective covering on the core ball, wherein the retro-reflective covering has an opening aligned with the mounting recess of the core ball, wherein the mounting recess includes one or more interior engagement structures for engaging one or more exterior engagement structures of a mounting post when the retro-reflective marker sphere is mounted on a mounting post, and wherein the retro-reflective covering is white-colored.

According to a twelfth broad aspect, the present invention provides a device comprising a retro-reflective marker sphere comprising: a core ball comprising: a generally spherical body portion, a mounting base extending from one end of the body portion of the core ball, and a mounting recess having a recess opening in the mounting base and extending into the body portion of the core ball, and a retro-reflective covering on the core ball, the retro-reflective covering comprising an opening through which the mounting base of the core ball extends, wherein the mounting recess includes one or more interior engagement structures for engaging one or more exterior engagement structures of a mounting post when the retro-reflective marker sphere is mounted on the mounting post, wherein a flat lower surface of the mounting base is spaced proximally from a lower edge of the opening of the retro-reflective covering, and wherein the mounting base has an alignment indicator on one or more sides of the mounting base.

According to a thirteenth broad aspect, the present invention provides a device comprising a retro-reflective marker sphere comprising: a core ball comprising: a generally spherical body portion, a mounting base extending from one end of the body portion of the core ball, and a mounting recess having a recess opening in the mounting base and extending into the body portion of the core ball, and a retro-reflective covering on the core ball, the retro-reflective covering comprising an opening through which the mounting base of the core ball extends, wherein the mounting recess includes one or more interior engagement structures for engaging one or more exterior engagement structures of a mounting post when the retro-reflective marker sphere is mounted on the mounting post, wherein a flat lower surface of the mounting base is spaced proximally from a lower edge of the opening of the retro-reflective covering, and wherein the mounting base has a polygonal cross-section in a plane perpendicular to an axis of the core ball.

According to a fourteenth broad aspect, the present invention provides a device comprising a retro-reflective marker sphere comprising: a core ball comprising: a generally spherical body portion, a mounting base extending from one end of the body portion of the core ball, and a mounting recess having a recess opening in the mounting base and extending into the body portion of the core ball, and a retro-reflective covering on the core ball, the retro-reflective covering comprising an opening through which the mounting base of the core ball extends, wherein the core ball is a single-piece core ball, wherein a flat lower surface of the mounting base is spaced proximally from a lower edge of the opening of the retro-reflective covering, and wherein the mounting recess includes an interior screw thread for engaging an exterior screw thread of a mounting post when the retro-reflective marker sphere is mounted on the mounting post.

BRIEF DESCRIPTION OF THE DRAWINGS

The accompanying drawings, which are incorporated herein and constitute part of this specification, illustrate exemplary embodiments of the present invention and, together with the general description given above and the detailed description given below, serve to explain the features of the present invention.

FIG. 13 is a bottom perspective view of a retro-reflective marker sphere according to one embodiment of the present invention.

FIG. 14 is a bottom perspective view of a retro-reflective marker sphere according to one embodiment of the present invention.

FIG. 15 is a bottom perspective view of a retro-reflective marker sphere according to one embodiment of the present invention.

FIG. 21 shows a blister strip of packaged retro-reflective marker spheres according to one embodiment of the present invention.

FIG. 22 is a cross-sectional view of a packaged retro-reflective marker sphere according to one embodiment of the present invention.

DETAILED DESCRIPTION OF THE PREFERRED EMBODIMENTS

Definitions

Figure 1:
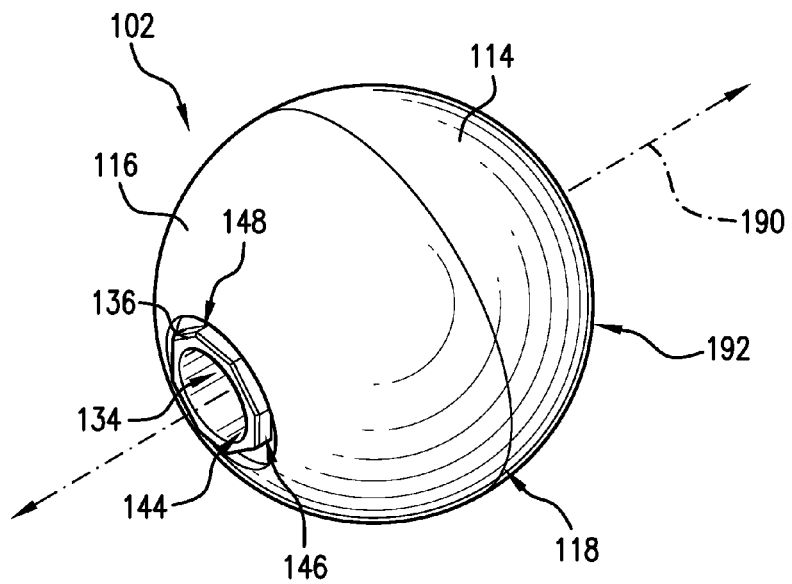
FIG. 1 is a perspective view of a retro-reflective marker sphere according to one embodiment of the present invention.
Figure 2:
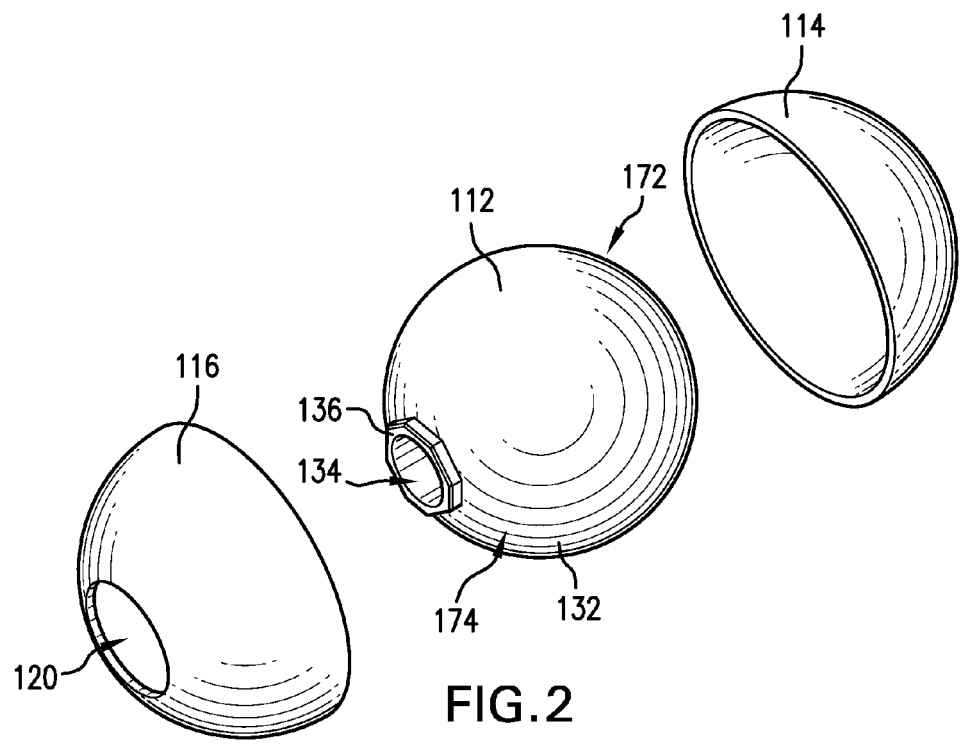
FIG. 2 is an exploded view of the retro-reflective marker sphere of FIG. 1, with divets in a core ball and interior structures in a mounting recess of the core ball of the retro-reflective marker sphere omitted for simplicity of illustration.

Where the definition of terms departs from the commonly used meaning of the term, applicant intends to utilize the definitions provided below, unless specifically indicated.

For purposes of the present invention, it should be noted that the singular forms, "a," "an" and "the," include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, the term "alignment indicator" refers to a symbol or other type of indicator on one or more sides of a mounting base of a retro-reflective marker sphere that may be used to determine if the retro-reflective marker sphere is aligned properly on its mounting post. Examples of alignment indicators include: lines, dots, letters, numbers, stars, shapes, etc.

For purposes of the present invention, the term "audible" refers to a sound that may be heard by an human being having normal hearing.

For purposes of the present invention, the term "backing layer" refer to the one or more layers of a blister pack joined to the pocket layer to thereby contain an item in the blister pack. If the backing layer has an opening, part of the item contained in the blister pack may protrude through the opening. Suitable materials for use as a backing layer include paper, cardboard, plastic, metal foil, such as aluminum foil, mylar, Tyvek® (flashspun high-density polyethylene fiber material manufactured by Dupont), etc. In some blister packs of the present invention, there may be two or more backing layers. For example, one backing layer may be made of cardboard, a stiff plastic, etc., to provide structural stability to the blister pack, and a second backing layer may be made of a metal foil that is rupturable.

For purposes of the present invention, the term "blister card" refers to a blister package comprising a connected two-dimensional set of blister packs.

For purposes of the present invention, the term "blister pack" refers to the common meaning of the term "blister pack," i.e., a package comprising a pocket formed of a formable material such as a plastic and one or more backing layers that seal the package. Examples of formable materials include thermoformable or thermosettable plastics.

For purposes of the present invention, the term "blister package" refers to a package comprising one or more blister packs.

For purposes of the present invention, the term "blister strip" refers to a blister package comprising a one-dimensional strip of blister packs.

For purposes of the present invention, the term "chrome-colored" refers to a bright silver mirrored reflective finish. Examples of chrome-colored retro-reflective coverings include tapes, inks, emergency reflective sign paints, emergency reflective road markings, etc.

For purposes of the present invention, the term "centipoise" refers to a unit of dynamic viscosity and is the amount of force necessary to move a layer of liquid in relation to another liquid. Centipoise is considered the standard unit of measurement for fluids of all types. It is one hundredth of a poise. Water at approximately 70° F. (21° C.) is about one centipoise. When determining centipoise, all other fluids are calibrated to the viscosity of water. Blood has a viscosity of 10 centipoise, and ethylene glycol has a viscosity of 15 centipoise.

For purpose of the present invention, the term "engage" refers to a contacting and/or interlocking interaction between two or more engagement structures.

For purposes of the present invention, the term "engagement structure" refers to a structure on a first object, such as a retro-reflective marker sphere or a post, that is shaped to engage one or more engagement structures on a second object, such as a post or a retro-reflective marker sphere. Examples of engagement structures include interior screw threads, exterior screw threads, ledges, tabs, recesses, rims, etc.

For purposes of the present invention, the term "exterior snap-on engagement structure" refers to an engagement structure on an exterior surface of an object, such as a mounting post. Examples of exterior snap-on engagement structures include the exterior screw thread in FIG. 12; the recess in the mounting post shown in FIGS. 38 and 39; etc.

For purposes of the present invention, the term "generally hemispherical" refers to an object, such as a retro-reflective marker sphere upper or lower retro-reflective covering, that is at least 50% hemispherical in shape over its surface. An object that is generally hemispherical in shape may include one or more openings and/or recesses. An object that is generally hemispherical in shape, such as a retro-reflective marker sphere upper or lower retro-reflective covering, may be comprised of one piece or two or more pieces. An object that is generally hemispherical in shape may be hollow or solid.

For purposes of the present invention, the term "generally spherical" refers to an object, such as a retro-reflective marker sphere covering or a core ball, that is at least 50% spherical in shape over its surface. An object that is generally spherical in shape may include one or more openings and/or recesses. An object that is generally spherical in shape, such as a retro-reflective marker sphere covering, may be comprised of one piece or two or more pieces. An object that is generally spherical in shape may be hollow or solid.

For purposes of the present invention, the term "gold-colored" refers to a bright gold reflective finish. Examples of gold-colored retro-reflective coverings include tapes, inks, paints for cars, bikes and motorcycles, decorative markings for cars, bikes and motorcycles, etc.

Figure 34:
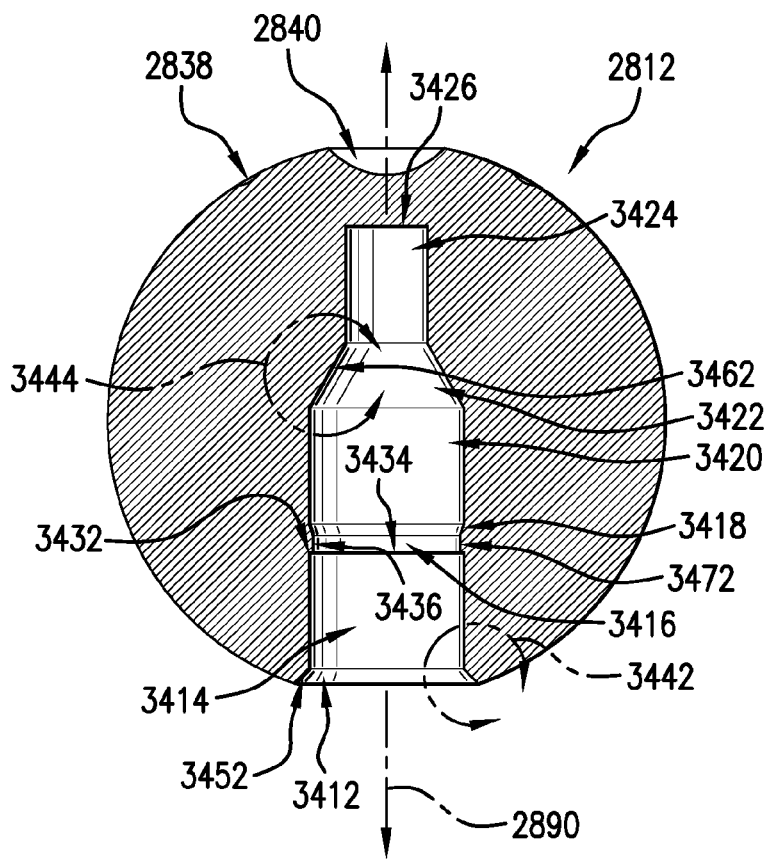
FIG. 34 is a cross-sectional view of the core ball of FIG. 32 taken along line B-B of FIG. 33.

For purposes of the present invention, the term "interior snap-on engagement structure" refers to an engagement structure on an interior surface or recess of an object, such as a retro-reflective marker sphere. Examples of interior snap-on engagement structures include the semi-locking interior screw thread shown in FIGS. 10, 11 and 12; the raised rim shown in FIGS. 34 and 39; etc.

For purposes of the present invention, the term "manually removable" refers to a pocket layer joined to a backing layer by an adhesive that has a peel strength of no greater than 5 lbs. (22.24 N) of force. In one embodiment of the present invention, a manually removable adhesive may have a peel strength of no greater than 3 lbs. (13.34 N) of force.

For purposes of the present invention, the terms "magnetic resonance imaging" (MRI), "nuclear magnetic resonance imaging" (NMRI), or "magnetic resonance tomography" (MRT) refer to a medical imaging technique used in radiology to visualize detailed internal structures. MRI makes use of the property of nuclear magnetic resonance (NMR) to image nuclei of atoms inside the body. An MRI machine uses a powerful magnetic field to align the magnetization of some atomic nuclei in the body, and radio frequency fields to systematically alter the alignment of this magnetization. This causes the nuclei to produce a rotating magnetic field detectable by the scanner. This information is recorded to construct an image of the scanned area of the body. Magnetic field gradients cause nuclei at different locations to rotate at different speeds. By using gradients in different directions 2D images or 3D volumes can be obtained in any arbitrary orientation. MRI provides good contrast between the different soft tissues of the body, which makes it especially useful in imaging the brain, muscles, the heart, and cancers compared with other medical imaging techniques such as computed tomography (CT) or X-rays. Unlike CT scans or traditional X-rays, MRI does not use ionizing radiation.

For purposes of the present invention, the term "non-rupturable material" refers to a material used as a backing layer for a blister pack that is not designed to be manually ruptured by a user.

For purposes of the present invention, the term "pocket layer" refers to the layer of a blister pack including a pocket or bubble. Examples of materials that may be used in pocket layers includes transparent or translucent plastics such as clear or colored polyvinyl chloride (PVC), rigid PVC, duplex structures such as PVC/PCTFE (polyvinyl chloride/polychlorotrifluoroethylene), triplex laminates such as PVC/PE/PCTFE (polyvinyl chloride/polyethylene/polychlorotrifluoroethylene), etc.

For purposes of the present invention, the term "polygon" without any modifier refers to both regular and irregular polygons. Similarly, an object that is "polygonal" in shape may be in the shape of a regular or an irregular polygon. For purposes of the present invention, a polygon or an object that is polygonal in shape may have rounded corners.

For purposes of the present invention, the term "proximal" refers to the direction toward the end of a retro-reflective marker sphere where a mounting base of the retro-reflective marker sphere is located, toward the base of a mounting post or toward the end of a medical device that is held by a user or that is used to mount the medical device in place. For purposes of the present invention, the term "distal" refers to the direction opposite the "proximal" direction.

For purposes of the present invention, the term "radiopaque" refers to an object, such as a retro-reflective marker sphere or a core ball, that blocks x-rays or other types of electromagnetic radiation such as UV (ultraviolet) light. A non-radiopaque material, such as a plastic, may be made radiopaque by adding a radiopaque dopant, such as barium, to the material. Examples of radiopaque materials that may be used as dopants to make radiopaque core balls and radiopaque retro-reflective marker spheres of the present invention include calcium phosphate cement, radiopaque polymer salts, iodine agents such as barium sulfate, metal agents such as tantalum, etc.

For purposes of the present invention, the term "retro-reflective" refers to the conventional meaning of the term "retro-reflective," i.e., an object or surface that reflects light back to its source with a minimum scattering of light. Retro-reflective materials such as retro-reflective tape and paint may be made in a variety of colors. For example, retro-reflective tapes and materials are commonly used in pavement marking tapes, transport trailer tapes, and safety markers or cones in colors such as white, yellow, red and orange.

For purposes of the present invention, the term "retro-reflective marker sphere" refers to a retro-reflective marker sphere that is retro-reflective and/or has a retro-reflective covering on at least part of the retro-reflective marker sphere. In some embodiments of the present invention, the retro-reflective covering covers at least 95% of the retro-reflective marker sphere.

For purposes of the present invention, the term "right-side-up orientation" refers to a retro-reflective marker sphere oriented in a blister pack so that the proximal end of the retro-reflective marker sphere is adjacent to the backing layer of the blister pack.

For purposes of the present invention, the term "rupturable material" refers to a material used as a backing layer for a blister pack that may be ruptured by a user pushing out a retro-reflective marker sphere enclosed in the blister pack through the backing layer, thereby allowing the retro-reflective marker sphere to be removed from the blister pack. Examples of rupturable materials include paper, cardboard, metal foils such as aluminum, some types of plastics, etc.

For purposes of the present invention, the term "semi-locking screw thread" refers to a first screw thread which includes a thread that has a ridge that does not fully mate with the groove of a second screw thread that engages the first screw thread.

For purposes of the present invention, the term "single-piece" refers to an object that is made of a single piece, as opposed to being made of two or more pieces.

For purposes of the present invention, the term "snap-on mounting post" refers to a mounting post that is designed to allow a snap-on retro-reflective marker sphere to be snapped onto the mounting post.

For purposes of the present invention, the term "snap-on retro-reflective marker sphere" refers to a retro-reflective marker sphere that snaps onto a mounting post of a medical device. The mounting post may be either a snap-on mounting post or a threaded mounting post. For example, in one embodiment, the present invention provides a retro-reflective marker sphere that is designed to be snapped onto a threaded mounting post.

For purposes of the present invention, the term "threaded mounting post" refers to a mounting post that includes one or more exterior screw threads that is designed to allow a retro-reflective marker sphere with a threaded mounting recess to be screwed onto the mounting post.

For purposes of the present invention, the term "threaded retro-reflective marker sphere" refers to a retro-reflective marker sphere that includes one or more interior screw threads in a mounting recess of the retro-reflective marker sphere.

For purposes of the present invention, the term "two-piece retro-reflective covering" refers to a retro-reflective covering that comprises only two pieces. Examples of two-piece retro-reflective coverings are shown in FIGS. 1, 2, 3, 4, 5, 6, 10, 28, 29, 30, 31, 32, 33, 34, 35 and 36.

For purposes of the present invention, the term "viscosity" refers to the measure of a fluid's resistance to flow and may be thought of as fluid friction. Thinner liquids, such as water, have lower viscosities, while thicker liquids like oil have higher viscosities.

For purposes of the present invention, the term "white-colored" refers to a white finish that reflects light back towards the source of the light. Examples of white-colored retro-reflective coverings include pavement marking tapes, transport trailer tapes, and safety markers or cones.

DESCRIPTION

Retro-reflective marker spheres, also referred to as passive reflective markers, are widely used in image guidance systems. For example, retro-reflective marker spheres have been used in military, entertainment, sports, and medical applications, and for validation of computer vision and robotics. In filmmaking, retro-reflective marker spheres have been used in recording actions of human actors and using that information to animate digital character models in 2D or 3D computer animation. In motion-capture sessions, movements of one or more actors are sampled many times per second, although with most techniques (recent developments from Weta Digital use images for 2D motion capture and project into 3D), motion capture records only the movements of the actor, not his or her visual appearance. This animation data is mapped to a 3D model so that the model performs the same actions as the actor. This is comparable to the older technique of rotoscope, such as that used in Ralph Bakshi's The Lord of the Rings (1978) and American Pop (1981) animated films in which the motion of an actor was filmed, and then the film was used as a guide for the frame-by-frame motion of a hand-drawn animated character. Camera movements may also be motion captured so that a virtual camera in the scene will pan, tilt, or dolly around the stage driven by a camera operator while the actor is performing, and the motion capture system can capture the camera and props as well as the actor's performance. This allows the computer-generated characters, images and sets to have the same perspective as the video images from the camera. A computer processes the data and displays the movements of the actor, providing the desired camera positions in terms of objects in the set. Retroactively obtaining camera movement data from the captured footage is known as match moving or camera tracking.

In medicine, one-time-use retro-reflective markers spheres are used to aid registration and instrument tracking during image guided surgery procedures such as neurological procedures, spin procedure and orthopedic procedures.

Typically, retro-reflective marker spheres have a high coefficient of retro-reflection on the external surface to provide feedback to the system/camera. These surfaces consist of micro glass spheres that reflect light. However, because medical retro-reflective marker spheres are often used within the sterile field, the spheres may need to be sterilized using processes such as ethylene oxide (ETO) gas sterilization, gamma-ray sterilization and electron beam (E-beam) sterilization. These sterilization processes may negatively impact polymers and may degrade the polymer structure. For this reason, for medical applications, retro-reflective marker spheres may need to be made of materials that are able to withstand the impact of sterilization.

Depending on the medical application, different numbers and arrangements of retro-reflective marker spheres may be mounted on various types of surgical tooling that may be used. For example, from two to five retro-reflective marker spheres may mounted on a surgical probe. Depending on the type of posts used on a particular surgical probe, each of the retro-reflective marker spheres is mounted on a surgical probes either by screwing the retro-reflective marker sphere onto a threaded mounting post of the surgical probe or by snapping the retro-reflective marker sphere onto a snap-on post of the surgical probe. Once mounted on a surgical problem, retro-reflective marker spheres provide an accuracy reference point for the surgical probe in three-dimensional space.

In one embodiment, the present invention provides a threaded sterile retro-reflective marker sphere that includes a mounting base for improved mounting on a threaded mounting post of a medical device used in image-guided surgical procedures. The retro-reflective marker sphere comprises an interior ball on which are mounted two retro-reflective hemispheres to form a spherical covering. A retro-reflective marker sphere includes a threaded mounting recess in the interior ball at one end into which a threaded mounting post of the medical device extends when the retro-reflective marker sphere is mounted on the medical device. The lower sphere includes an opening aligned with a mounting recess in the interior core ball. Conventionally, the interior screw thread in the mounting recess of a retro-reflective marker sphere is used to determine the point at which the retro-reflective marker sphere is fully mounted on a threaded mounting post. The retro-reflective marker sphere is considered fully mounted when the retro-reflective marker sphere can be turned no more on a threaded mounting post of a medical device. The mounting recess of a conventional retro-reflective marker sphere includes a thread along the entire length of the mounting recess. In contrast, in one embodiment of the present invention, the interior core ball includes a mounting base that extends beyond the edge of the bottom hemisphere so that the mounting base is the only part of the retro-reflective maker sphere that contacts the base of the threaded mounting post. In one embodiment of the present invention, a retro-reflective marker sphere includes a mounting recess having an interior screw thread to allow the retro-reflective marker sphere to be mounted on threaded mounting post, but the interior screw thread does not extend all the way to the top of the mounting recess. A non-threaded portion of the mounting recess is used for alignment of the retro-reflective marker sphere in the axial direction of the threaded mounting post.

Figure 3:
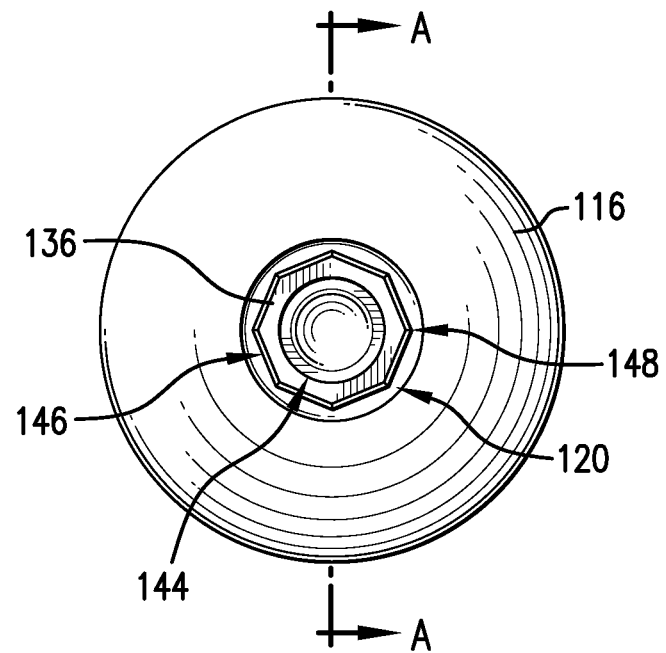
FIG. 3 is a bottom plan view of the retro-reflective marker sphere of FIG. 1.
Figure 4:
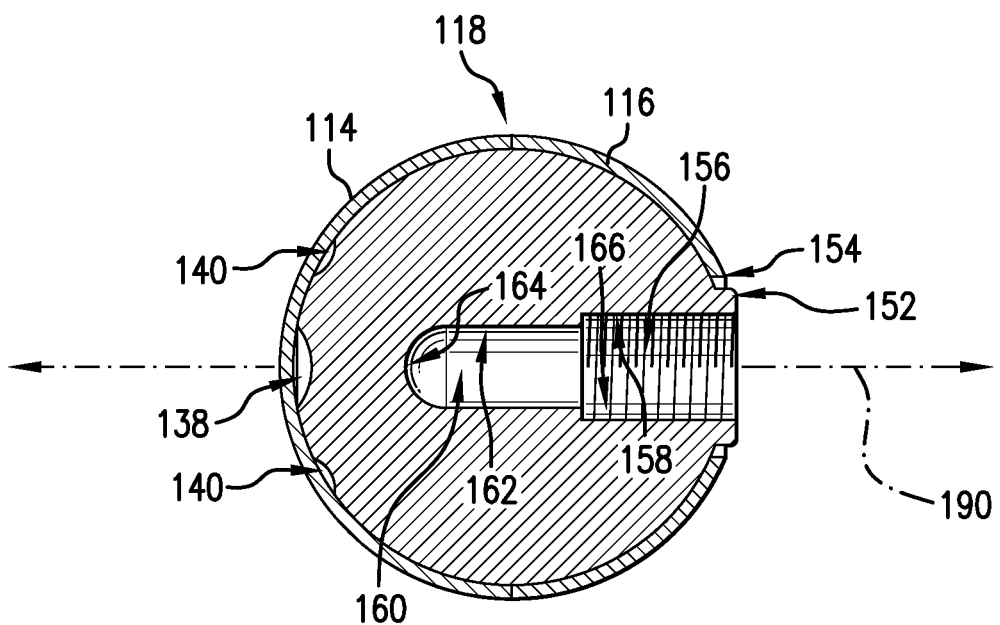
FIG. 4 is a cross-sectional view of the retro-reflective marker sphere of FIG. 1 taken along line A-A of FIG. 3.
Figure 5:
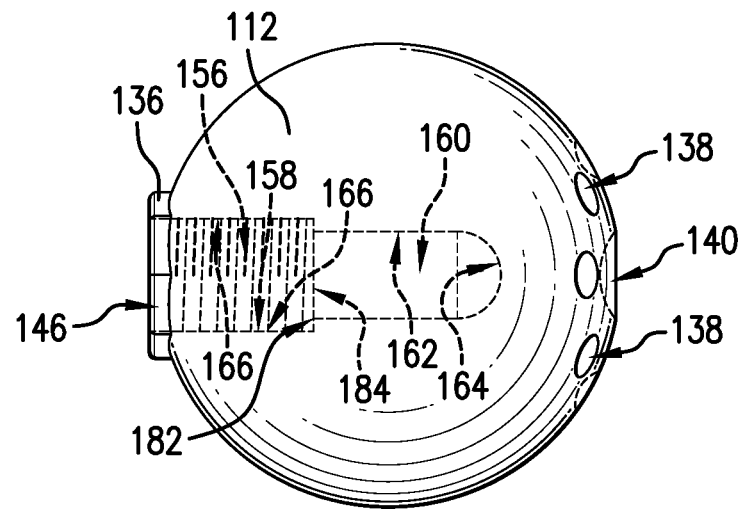
FIG. 5 is a side view of the core ball of the retro-reflective marker sphere of FIG. 1.
Figure 6:
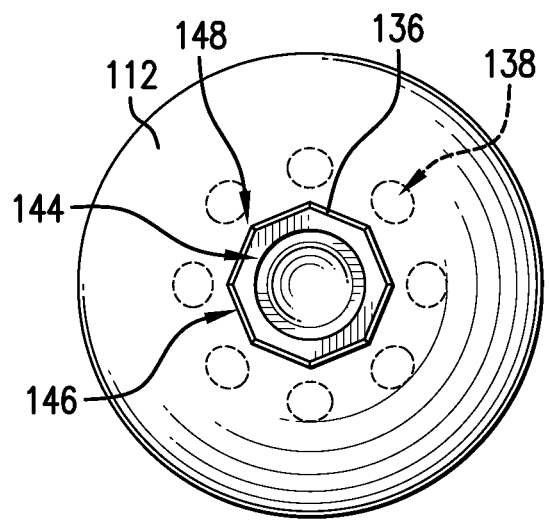
FIG. 6 is a bottom plan view of the core ball of FIG. 5.

FIGS. 1, 2, 3 and 4 show a retro-reflective marker sphere 102 according to one embodiment of the present invention. Retro-reflective marker sphere 102 comprises a core ball 112 on which is mounted an upper retro-reflective covering piece 114 and a lower retro-reflective covering piece 116. Upper retro-reflective covering piece 114 and lower retro-reflective covering piece 116 are generally hemispherical in shape. Where upper retro-reflective covering piece 114 and lower retro-reflective covering piece 116 meet there is a seam 118. Lower retro-reflective covering piece 116 includes a circular opening 120. Core ball 112, shown in detail in FIGS. 5 and 6, has a generally spherical body portion 132, a mounting recess 134, a mounting base 136, an upper central circular (dimple) divet 138 and eight upper peripheral circular (dimples) divets 140. Mounting recess 134 is circular in cross-section and has a circular opening 144 centered in mounting base 136. Mounting base 136 is octagonal in shape, i.e., mounting base 136 has eight sides 146 and eight corners 148. When assembled, as shown in FIGS. 1, 3 and 4, mounting base 136 extends through circular opening 120 of lower retro-reflective covering piece 116 so that a lower surface 152 of mounting base 136 is spaced proximally from a lower edge 154 of circular opening 120 and lower retro-reflective covering piece 116. Mounting recess 134 includes a recess lower portion 156 having a cylindrical wall 158, a recess upper portion 160 having a cylindrical wall 162 and a rounded upper end 164. Recess lower portion 156 includes an interior screw thread 166 on cylindrical wall 158. Recess lower portion 156 is larger in diameter than recess upper portion 160. Recess upper portion 160 does not have an interior screw thread. Recess lower portion 156 and recess upper portion 160 each have a circular cross-section. In the embodiment shown, upper retro-reflective covering piece 114 covers an upper half 172 of core ball 112, and lower retro-reflective covering piece 116 covers a lower half 174 of core ball 112. A circular ledge 182 is formed at an upper end 184 of recess lower portion 156 due to the fact that recess lower portion 156 is larger in diameter than recess upper portion 160. Retro-reflective marker sphere 102 and core ball 112 have an axis shown by double-headed dashed arrow 190, shown in FIGS. 1 and 4, that extends through the center of mounting recess 134. Together, upper retro-reflective covering piece 114 and lower retro-reflective covering piece 116 form a retro-reflective covering 192 that is generally spherical in shape.

Figure 7:
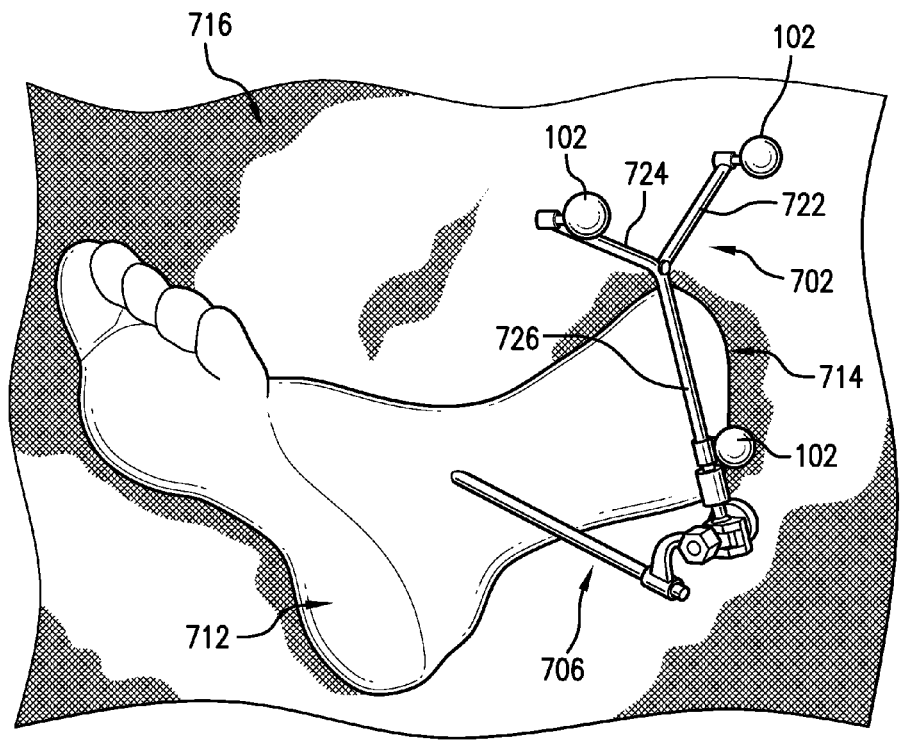
FIG. 7 is a perspective view of a medical device, mounted on a human foot, on which are mounted retro-reflective marker spheres according to one embodiment of the present invention.

FIG. 7 shows a medical device 702 on which are mounted three retro-reflective marker spheres 102. Medical device 702 is mounted by a mounting device 706 on a human foot 712 extending through an opening 714 in a covering blanket 716. Medical device 702 includes three arms 722, 724 and 726.

In FIG. 7, the three retro-reflective marker spheres provide a precise location in three-dimensional space of the contact area between the probe and the foot of the patient. The position of each of the retro-reflective marker spheres is registered using the vision system which extrapolates the position of probe relative to the foot of the patient.

Figure 8:
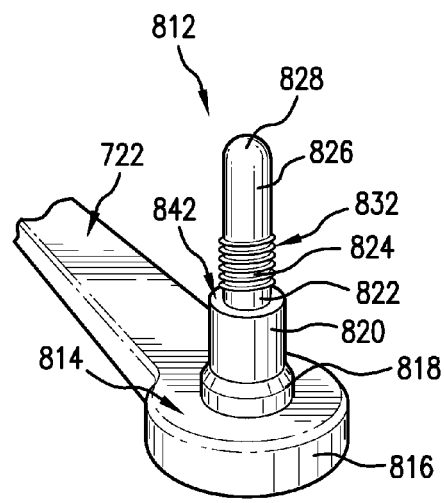
FIG. 8 is a perspective view of a threaded mounting post on an arm of the medical device of FIG. 7.

FIG. 8 shows a mounting post 812 that is mounted on an upper surface 814 of a circular end 816 of arm 722 of medical device 702. Mounting post 812 includes a post base 818, a cylindrical post lower portion 820, a post neck portion 822, a post middle portion 824, a cylindrical post upper portion 826 and a post rounded end 828. Post middle portion 824 includes an exterior screw thread 832. Post lower portion 820 includes an upper surface 842.

Figure 9:
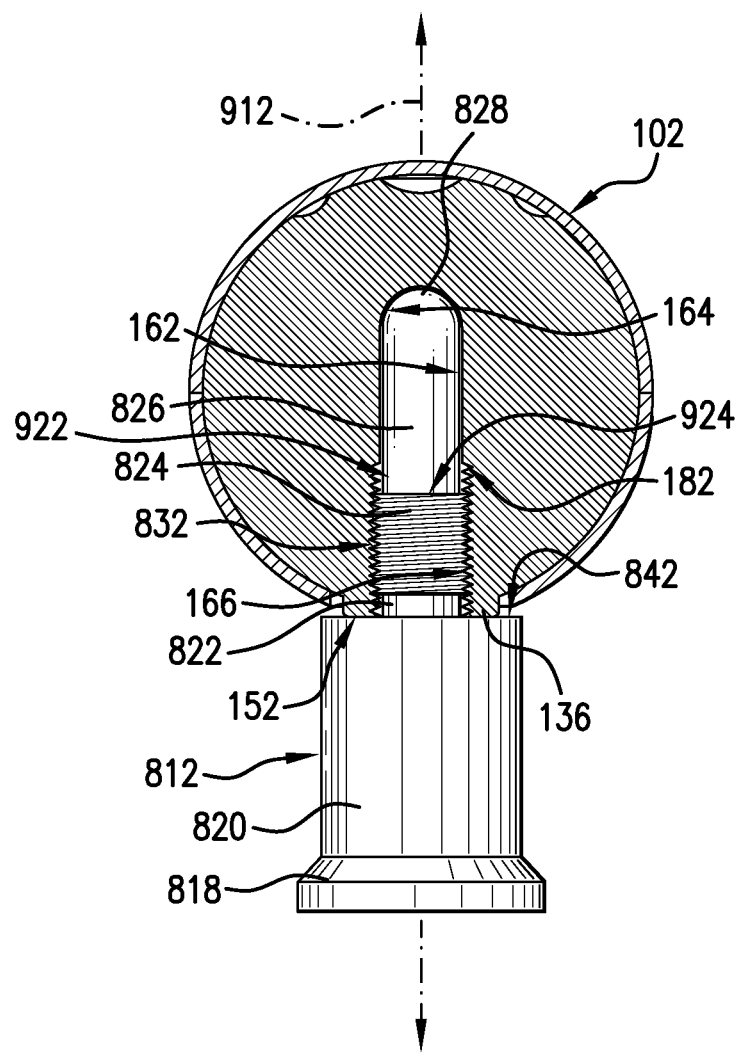
FIG. 9 is a cross-sectional view of the retro-reflective marker sphere of FIG. 1 mounted on the threaded mounting post of FIG. 8.

FIG. 9 shows retro-reflective marker sphere 102 mounted on mounting post 812. Interior screw thread 166 of retro-reflective marker sphere 102 screws onto exterior screw thread 832. Lower surface 152 of mounting base 136 abuts upper surface 842 of post lower portion 820, thereby ensuring that retro-reflective marker sphere 102 is mounted properly on mounting post 812. Post upper portion 826 and post rounded end 828 are received by recess upper portion 160 and rounded upper end 164, respectively, of mounting recess 134 of retro-reflective marker sphere 102 to help maintain the alignment of retro-reflective marker sphere 102 on mounting post 812 in the direction shown by double-headed arrow 912, i.e., the axial direction for mounting post 812. A gap 922 is formed between a top 924 of exterior screw thread 832 and ledge 182 due to lower surface 152 of mounting base 136 abutting upper surface 842 of post lower portion 820 prior to exterior screw thread 832 travelling fully upward in interior screw thread 166.

Figure 10:
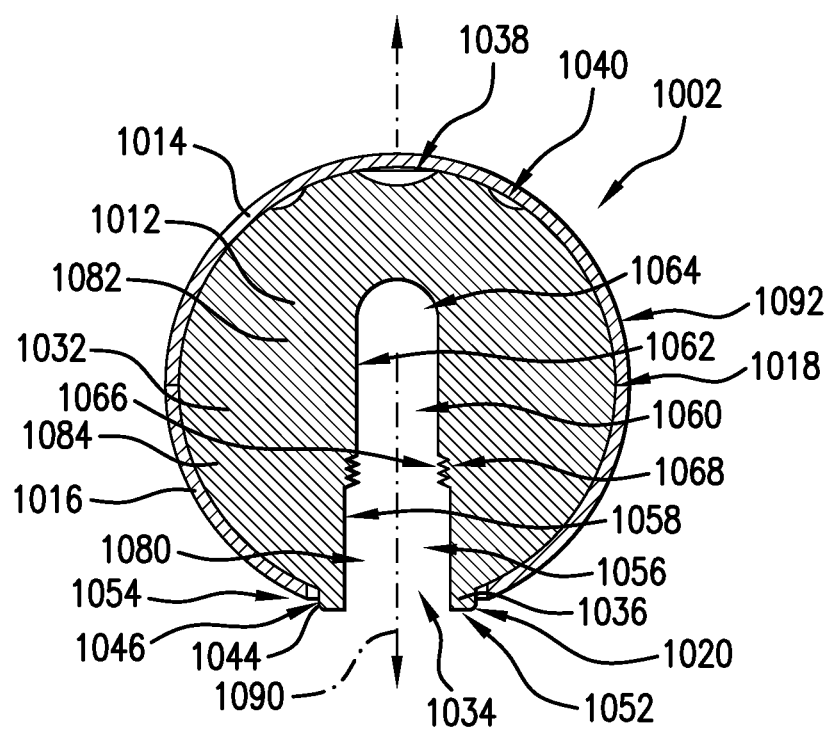
FIG. 10 is a cross-sectional view of a snap-on retro-reflective marker sphere according to one embodiment of the present invention.
Figure 11:
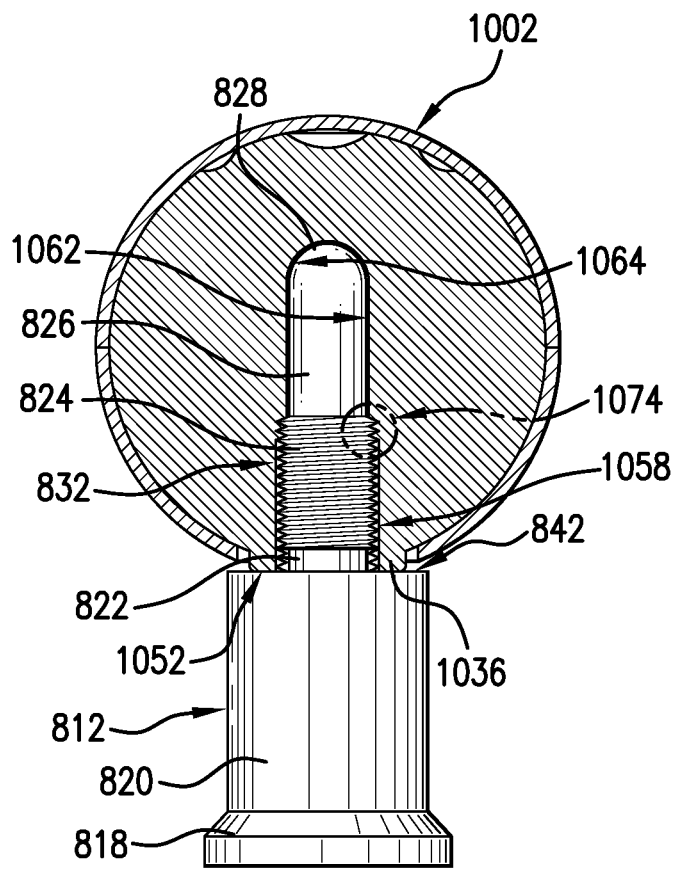
FIG. 11 is a cross-sectional view of the snap-on retro-reflective marker sphere mounted on the threaded mounting post of FIG. 8.
Figure 12:
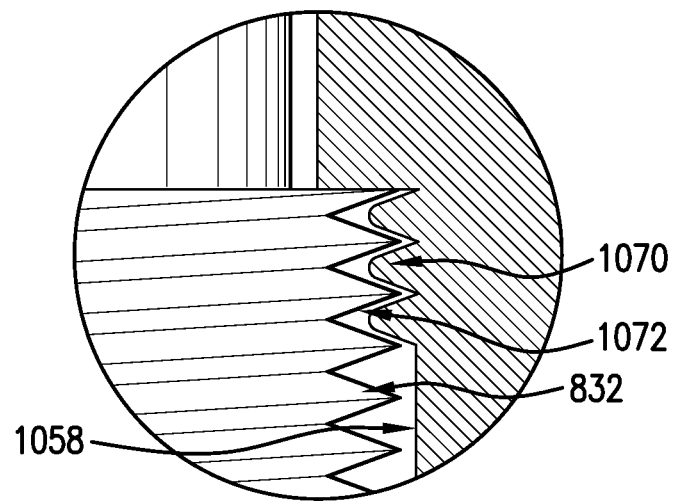
FIG. 12 is a close-up view of the dashed-circled region of FIG. 11.

FIG. 10 shows a retro-reflective marker sphere 1002 according to one embodiment of the present invention that may be snapped onto mounting post 812 as shown in FIGS. 11 and 12. Retro-reflective marker sphere 1002 comprises a core ball 1012 on which is mounted an upper retro-reflective covering piece 1014 and a lower retro-reflective covering piece 1016. Upper retro-reflective covering piece 1014 and lower retro-reflective covering piece 1016 are generally hemispherical in shape. Where upper retro-reflective covering piece 1014 and lower retro-reflective covering piece 1016 meet there is a seam 1018. Lower retro-reflective covering piece 1016 includes a circular opening 1020. Core ball 1012 has a generally spherical body portion 1032, a mounting recess 1034, a mounting base 1036, an upper central circular (dimple) divet 1038 and eight upper peripheral circular (dimples) divets 1040. Mounting recess 1034 is circular in cross-section and has a circular opening 1044 centered in mounting base 1036. Mounting base 1036 is octagonal in shape, i.e., mounting base 1036 has eight sides 1046 and eight corners (not shown). Mounting base 1036 extends through circular opening 1020 of lower retro-reflective covering piece 1016 so that a lower surface 1052 of mounting base 1036 is spaced proximally from a lower edge 1054 of circular opening 1020 and lower retro-reflective covering piece 1016. Mounting recess 1034 includes a recess lower portion 1056 having a cylindrical wall 1058, a recess upper portion 1060 having a cylindrical wall 1062 and a rounded upper end 1064. Recess lower portion 1056 includes a semi-locking interior screw thread 1066 at an upper end 1068 of recess lower portion 1056. Semi-locking interior screw thread 1066 is "semi-locking" because semi-locking interior screw thread 1066 has a rounded ridge 1070 that does not fully mate with groove 1072 of exterior screw thread 832 of mounting post 812, as shown in FIG. 12. The interaction of semi-locking interior screw thread 1066 and exterior screw thread 832 of mounting post 812, shown in detail in FIG. 12 corresponding to dashed-circled region 1074 of FIG. 11, causes an audible "snap" when retro-reflective marker sphere 1002 is snapped onto mounting post 812.

A lower section 1080 of recess lower portion 1056 does not include a screw thread to allow retro-reflective marker sphere 1002 to be snapped onto mounting post 812. Recess lower portion 1056 is larger in diameter than recess upper portion 1060. Recess upper portion 1060 does not have an interior screw thread. Recess lower portion 1056 and recess upper portion 1060 each have a circular cross-section. In the embodiment shown, upper retro-reflective covering piece 1014 covers an upper half 1082 of core ball 1012, and lower retro-reflective covering piece 1016 covers a lower half 1084 of core ball 1012. Retro-reflective marker sphere 1002 and core ball 1012 have an axis shown by double-headed dashed arrow 1090 in FIG. 10 that extends through the center of mounting recess 1034. Together, upper retro-reflective covering piece 1014 and lower retro-reflective covering piece 1016 form a retro-reflective covering 1092 that is generally spherical in shape.

Although in the embodiment of the present invention shown in FIGS. 1, 2, 3, 4, 5 and 6 the mounting base is octagonal in shape, i.e., the mounting base has an octagonal-shaped cross-section in a plane perpendicular to the axis of the retro-reflective marker sphere and the core ball, the mounting base may have various shapes such as circular, oval, triangular, star-shaped, square, rectangular, pentagonal, hexagonal, etc. In some embodiments of the present invention, the mounting base may be a shape such as a square, rectangle, pentagon, hexagon, octagon, etc., which has corners that allow for more precise molding of the core ball. For example, the corners/edges prevent the core ball from turning in an injection mold. The corners/edges also prevent counter-rotation of the core ball during unscrewing of a core pin used in forming the threaded mounting recess during injection molding.

Although in the embodiments described above and shown in the drawings, the sides of the mounting base are straight, in other embodiments the sides of the mounting base may be curved in either a convex or concave fashion. Also, even when the sides of mounting base are curved, the sides may still meet at corners.

In some embodiments of the present invention, the corners of the mounting base may be formed by one or more rectangular spokes or by triangular points that radiate from one or more sides of a mounting base that is otherwise polygonal, circular or oval in shape. In one embodiment of the present invention the rectangular spokes may radiate from the mounting base like the four arms of a plus sign, the six arms of an asterisk, etc. In one embodiment of the present invention, the triangular points may radiate from the sides of the mounting base like the points of a four, five, six, seven, eight, etc. pointed star.

FIG. 13 shows a retro-reflective marker sphere 1302 according to one embodiment of the present invention which includes mounting base 1312 that is triangular in shape, i.e., mounting base 1312 has three sides 1314 and three corners 1316. In the center of mounting base 1312 is a mounting recess 1322 that is similar to mounting recess 134. FIG. 14 shows a retro-reflective marker sphere 1402 according to one embodiment of the present invention which includes mounting base 1412 that is square in shape. Mounting base 1412 has four sides 1414 and four corners 1416. In the center of mounting base 1412 is a mounting recess 1422 that is similar to mounting recess 134. FIG. 15 shows a retro-reflective marker sphere 1502 according to one embodiment of the present invention which includes mounting base 1512 that is hexagonal in shape. Mounting base 1512 has six sides 1514 and six corners 1516. In the center of mounting base 1512 is a mounting recess 1522 that is similar to mounting recess 134. Other than the shapes of their respective mounting bases 1312, 1412 and 1512, retro-reflective marker spheres 1302, 1402 and 1502 are identical to retro-reflective marker sphere 102.

Figure 16:
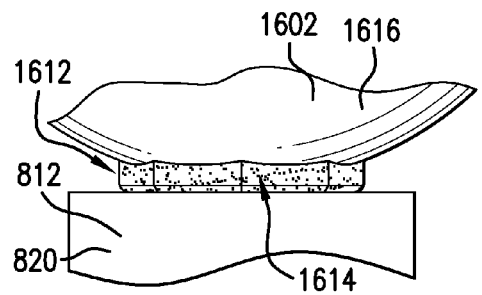
FIG. 16 shows a retro-reflective marker sphere mounting base having a contrasting color with respect to a retro-reflective covering of the retro-reflective marker sphere according to one embodiment of the present invention.

In some embodiments of the present invention, the mounting base of the retro-reflective marker sphere may include one or more alignment indicators. For example, FIGS. 16, 17, 18, 19 and 20 show examples of some of the types of alignment indicators that may be used to determine if a retro-reflective marker sphere is aligned properly on a mounting post. FIG. 16 shows a retro-reflective marker sphere 1602 according to one embodiment of the present invention having an octagonal-shaped mounting base 1612 that has a bright contrasting color shown by a pattern 1614 in comparison with a retro-reflective covering 1616 of retro-reflective marker sphere 1602 that may be easily seen by a user. The bright contrasting color functions as an alignment indicator, allowing the proper alignment of retro-reflective marker sphere 1602 on post lower portion 820 of mounting post 812 to be confirmed by the person mounting retro-reflective marker sphere 1602 on mounting post 812.

Figure 17:
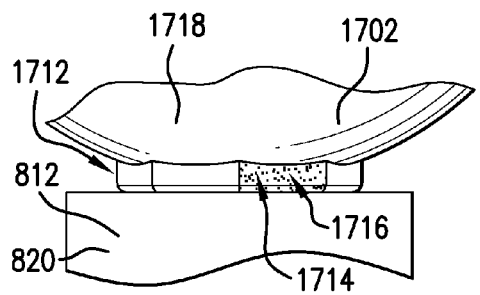
FIG. 17 shows a retro-reflective marker sphere mounting base with one side having a contrasting color with respect to a retro-reflective covering of the retro-reflective marker sphere according to one embodiment of the present invention.

FIG. 17 shows a retro-reflective marker sphere 1702 according to one embodiment of the present invention having an octagonal-shaped mounting base 1712 with a side 1714 that has a bright contrasting color, shown by a pattern 1716, in comparison with a retro-reflective covering 1718 of retro-reflective marker sphere 1702 and thus functions as an alignment indicator. The bright contrasting color allows the proper alignment of retro-reflective marker sphere 1702 on post lower portion 820 of mounting post 812 to be confirmed by the person mounting retro-reflective marker sphere 1702 on mounting post 812.

In one embodiment, the "bright contrasting color" is a variation in the substance with respect to light reflected by one or more sides of the mounting base. The contrasting color may be observed visually and/or by measurement of hue, saturation and brightness of the reflected light from the one or more sides of the mounting base.

Figure 18:
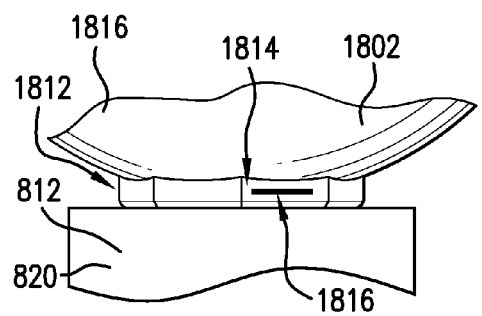
FIG. 18 shows a retro-reflective marker sphere mounting base having an alignment line on one side according to one embodiment of the present invention.

FIG. 18 shows a retro-reflective marker sphere 1802 according to one embodiment of the present invention having an octagonal-shaped mounting base 1812 with a side 1814 having an alignment line 1816 that has a bright contrasting color in comparison with a retro-reflective covering 1818 of retro-reflective marker sphere 1802 and thus functions as an alignment indicator. The bright contrasting color allows the proper alignment of retro-reflective marker sphere 1802 on post lower portion 820 of mounting post 812 to be confirmed by the person mounting retro-reflective marker sphere 1802 on mounting post 812.

Figure 19:
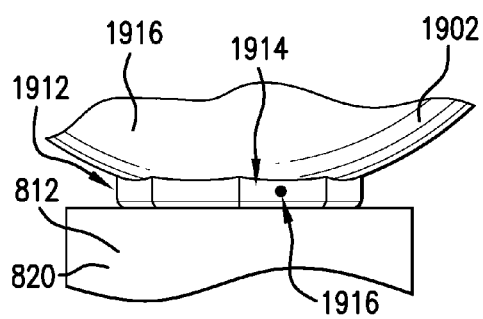
FIG. 19 shows a retro-reflective marker sphere mounting base having an alignment dot on one side according to one embodiment of the present invention.

FIG. 19 shows a retro-reflective marker sphere 1902 according to one embodiment of the present invention having an octagonal-shaped mounting base 1912 with a side 1914 having an alignment dot 1916 that has a bright contrasting color in comparison with a retro-reflective covering 1918 of retro-reflective marker sphere 1902 and thus functions as an alignment indicator. The bright contrasting color allows the proper alignment of retro-reflective marker sphere 1902 on post lower portion 820 of mounting post 812 to be confirmed by the person mounting retro-reflective marker sphere 1902 on mounting post 812.

Figure 20:
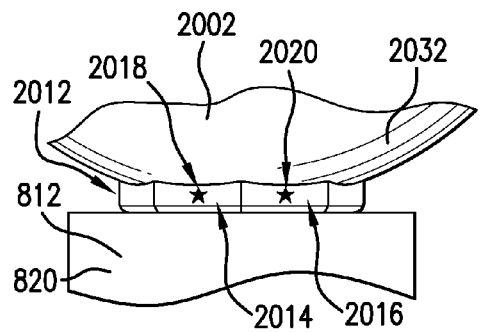
FIG. 20 shows a retro-reflective marker sphere mounting base having alignment stars on at least two sides according to one embodiment of the present invention.

FIG. 20 shows a retro-reflective marker sphere 2002 according to one embodiment of the present invention having an octagonal-shaped mounting base 2012 with sides 2014 and 2016 having respective alignment stars 2018 and 2020 that each have a bright contrasting color in comparison with a retro-reflective covering 2032 of retro-reflective marker sphere 2002 and thus function as alignment indicators. The bright contrasting color allows the proper alignment of retro-reflective marker sphere 2002 on post lower portion 820 of mounting post 812 to be confirmed by the person mounting retro-reflective marker sphere 2002 on mounting post 812.

FIG. 21 shows a blister strip 2102 comprising ten blister packs 2112 according to one embodiment of the present invention. Enclosed in each blister pack 2112 is one retro-reflective marker sphere 102. Blister strip 2102 includes a transparent or translucent pocket layer 2122 and a backing layer 2124 joined to pocket layer 2122. Pocket layer 2122 includes dome-shaped pockets 2132 and flat portions 2134. The presence of pockets 2132 forms openings 2136 that are each slightly larger in diameter than each retro-reflective marker sphere 102. Each blister pack 2112 is separated from one or two adjacent blister packs 2112 by a perforation 2142 that extends at least through pocket layer 2122 and may extend through backing layer 2124. Perforation 2142 allows neighboring blister packs 2112 to be separated from each other by a user tearing pocket layer 2122 and backing layer 2124 along a perforation 2142 between neighboring blister packs 2112. FIG. 22 shows a cross-section of one retro-reflective marker sphere 102 in a blister pack 2112.

Although FIG. 21 shows a blister strip used with one particular type of retro-reflective marker sphere, the blister strips of the present invention may be used with various types of retro-reflective marker spheres, including retro-reflective marker spheres for both threaded and snap-on mounting posts.

Figure 23:
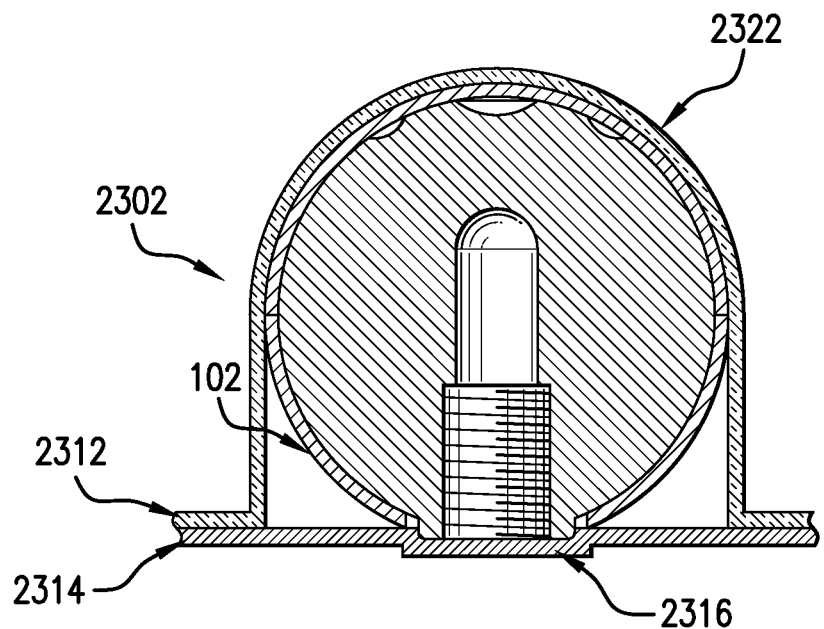
FIG. 23 is a cross-sectional view of a packaged retro-reflective marker sphere according to one embodiment of the present invention.
Figure 24:
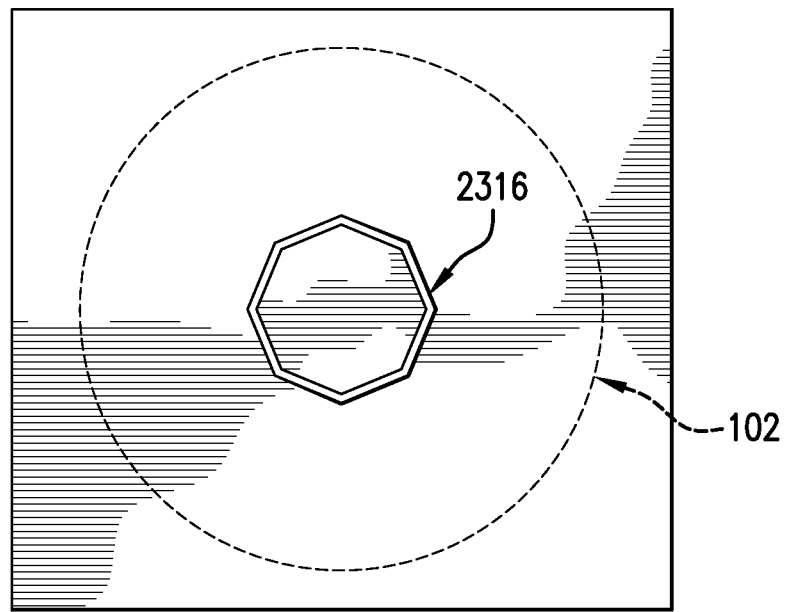
FIG. 24 is a bottom plan view of the packaged retro-reflective marker sphere of FIG. 23.

FIGS. 23 and 24 show a retro-reflective marker sphere 102 in a blister pack 2302 according to one embodiment of the present invention comprising a transparent or translucent pocket layer 2312 and a backing layer 2314 joined to pocket layer 2312. Backing layer 2314 includes an octagonal-shaped recessed portion 2316. Pocket layer 2312 includes a dome-shaped pocket 2322. Mounting base 136 fits into octagonal-shaped recessed portion 2316 to thereby help keep retro-reflective marker sphere 102 in a right-side-up orientation in blister pack 2302. Pocket 2322 contains retro-reflective marker sphere 102. A series of blister packs 2302 may be part of a blister strip similar to blister strip 2102.

Although the recess shown in FIGS. 23 and 24 is octagonal-shaped, the recess in the backing layer of the present invention may have various shapes including circular, oval, lozenge-shaped, etc., as well as various polygonal shapes.

Figure 25:
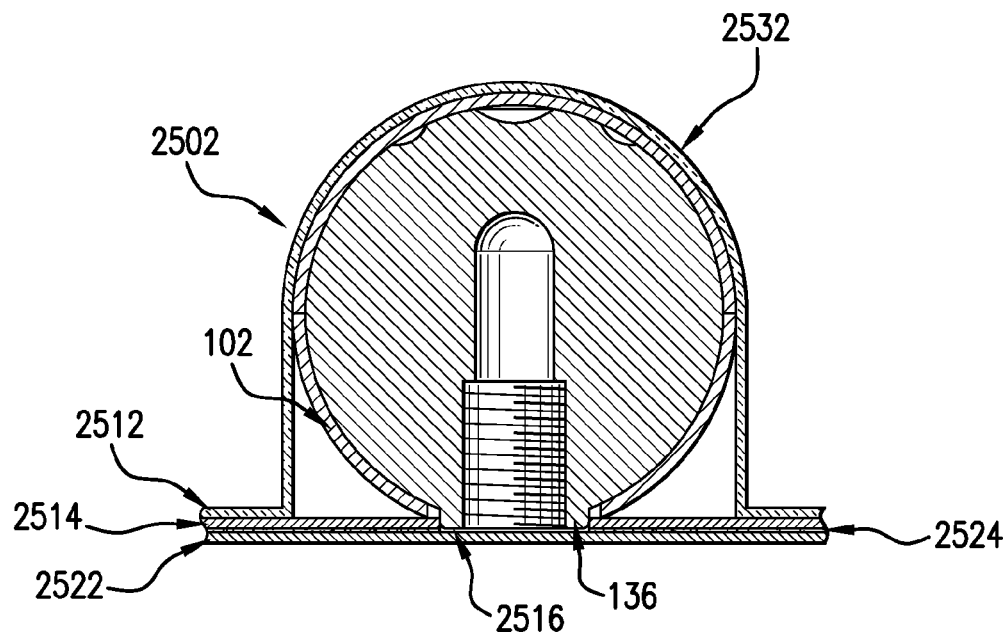
FIG. 25 is a cross-sectional view of a packaged retro-reflective marker sphere according to one embodiment of the present invention.
Figure 26:
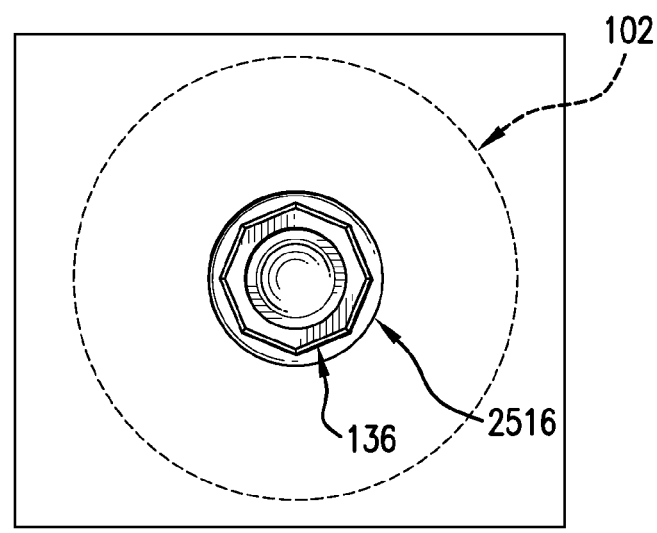
FIG. 26 is a bottom plan view of the packaged retro-reflective marker sphere of FIG. 25.

FIGS. 25 and 26 show a retro-reflective marker sphere 102 in a blister pack 2502 according to one embodiment of the present invention comprising a transparent or translucent pocket layer 2512 and a backing layer 2514 joined to pocket layer 2512. Backing layer 2514 includes a circular-shaped opening 2516. Mounting base 136 extends through circular-shaped opening 2516 to thereby help keep retro-reflective marker sphere 102 in right-side-up orientation in blister pack 2502. FIG. 25 shows a protective layer 2522 that is joined to backing layer 2514 to protect mounting base 136. Protective layer 2522 is joined to backing layer 2514 using an adhesive 2524. Adhesive 2524 may not be present in the region beneath mounting base 136 to avoid adhesive 2524 possibly sticking to mounting base 136. Adhesive 2524 on protective layer 2522 is sufficiently weak to allow protective layer 2522 to be removed from backing layer 2514. Once protective layer 2522 is removed from backing layer 2514, retro-reflective marker sphere 102 may be screwed onto a mounting post, such as mounting post 812 (not shown in FIGS. 25 and 26), while still in blister pack 2502. Retro-reflective marker sphere 102 may then be removed from blister pack 2502. Pocket layer 2512 includes a dome-shaped pocket 2532 that contains retro-reflective marker sphere 102. A series of blister packs 2502 may be part of a blister strip similar to blister strip 2102.

In one embodiment of the present invention, a user may screw retro-reflective marker sphere 102 onto a mounting post by grasping retro-reflective marker sphere 102 through pocket 2532 and turning retro-reflective marker sphere 102 on the thread of the mounting post.

Although the opening in the backing layer in FIGS. 25 and 26 is circular, the opening could be octagonal in shape, to match the shape of the mounting base of the retro-reflective marker sphere, or any other shape, such as oval, lozenge-shaped, etc.

Figure 27:
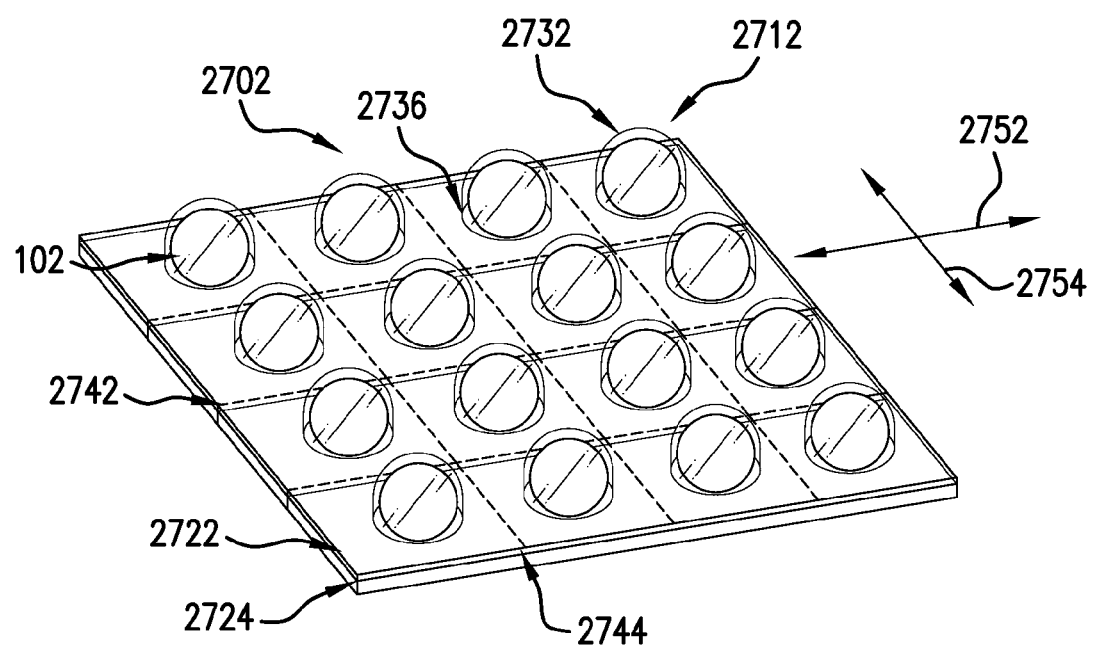
FIG. 27 shows a blister card of packaged retro-reflective marker spheres according to one embodiment of the present invention.
Figure 28:
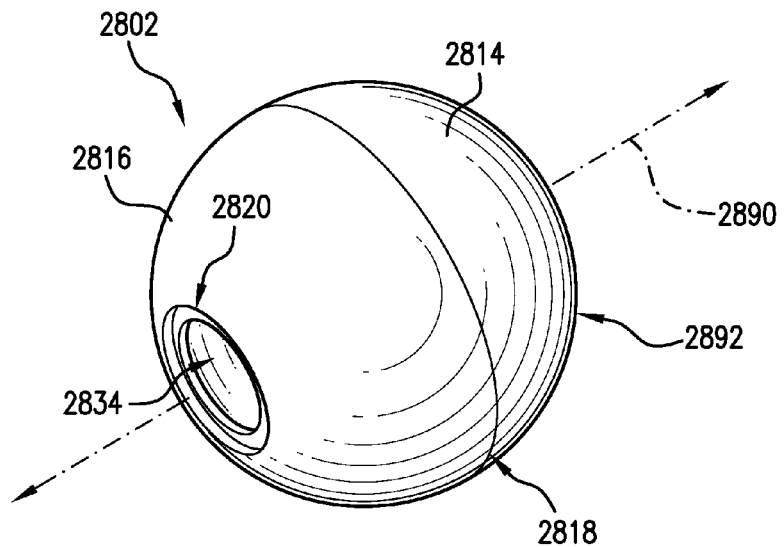
FIG. 28 is a perspective view of a retro-reflective marker sphere that may be used in various embodiments of the present invention.
Figure 29:
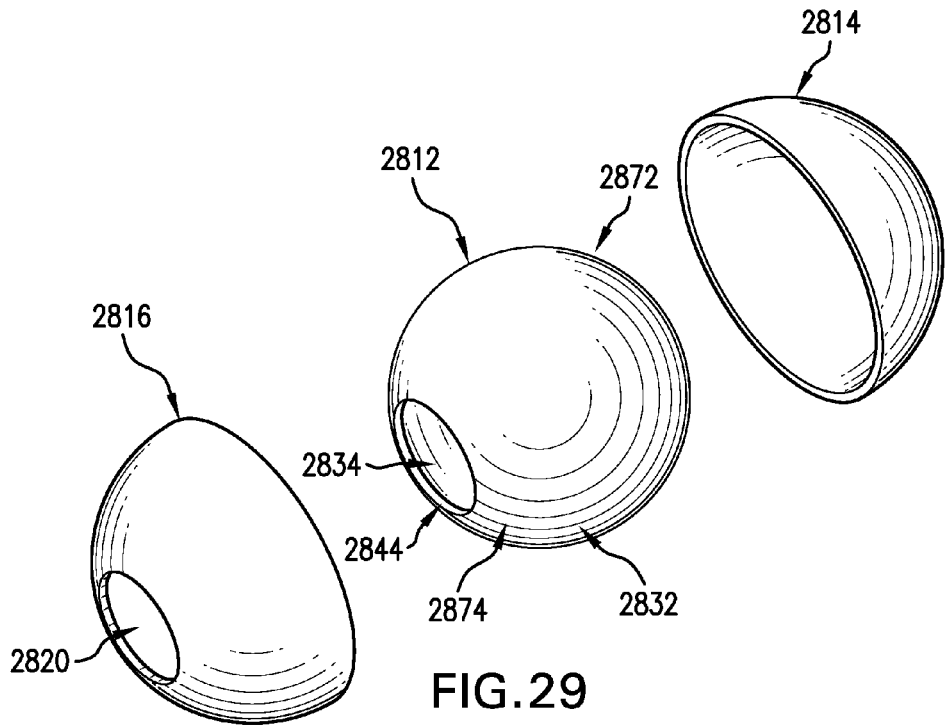
FIG. 29 is an exploded view of the retro-reflective marker sphere of FIG. 28, with divets in a core ball and interior structures in a mounting recess of the core ball of the retro-reflective marker sphere omitted for simplicity of illustration.
Figure 30:
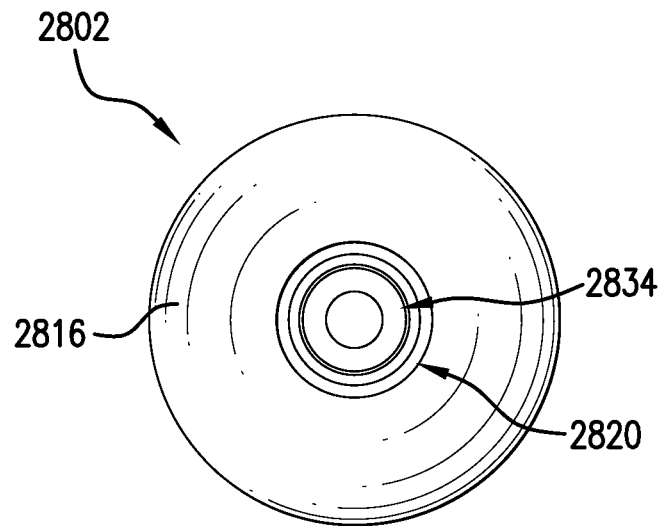
FIG. 30 is a bottom plan view of the retro-reflective marker sphere of FIG. 28.
Figure 31:
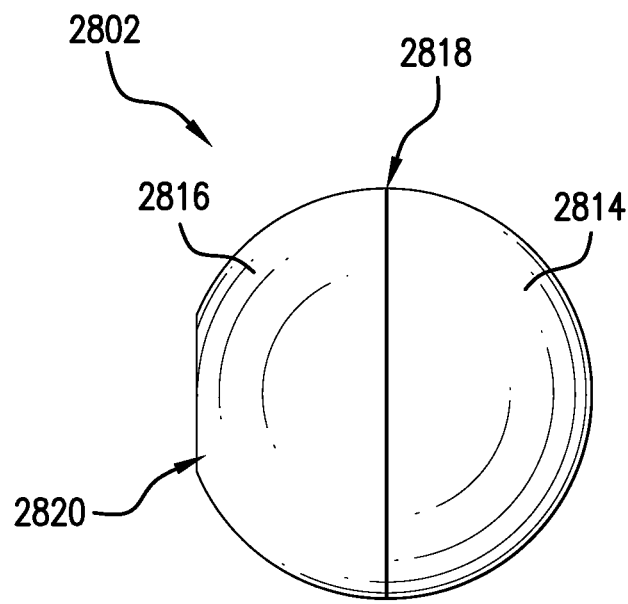
FIG. 31 is a side view of the retro-reflective marker sphere of FIG. 28.
Figure 32:
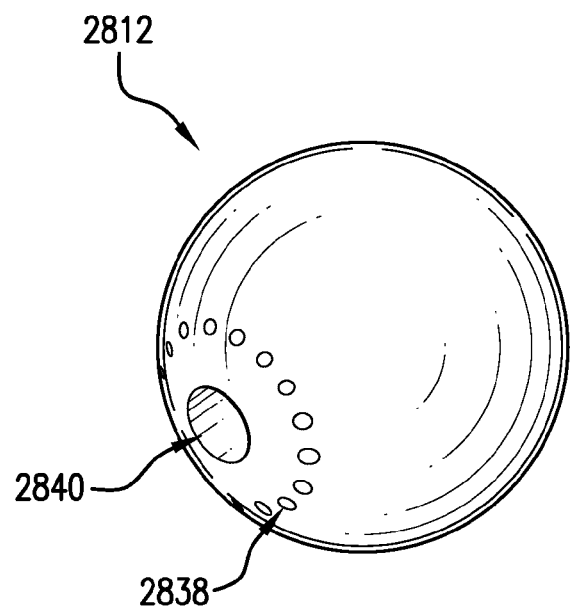
FIG. 32 is a perspective view of the core ball of the retro-reflective marker sphere of FIG. 28.
Figure 33:
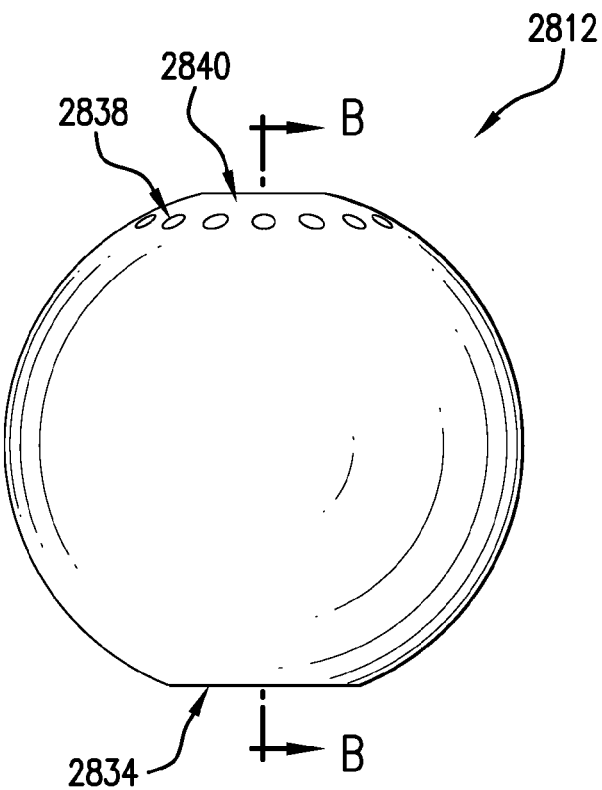
FIG. 33 is a side view of the core ball of FIG. 32.

FIG. 27 shows a 4×4 blister card 2702 comprising sixteen blister packs 2712 according to one embodiment of the present invention. Enclosed in each blister pack 2712 is one retro-reflective marker sphere 102. Blister card 2702 includes a transparent or translucent pocket layer 2722 and a backing layer 2724 joined to pocket layer 2722. Pocket layer 2722 includes dome-shaped pockets 2732 and flat portions 2734. The presence of pockets 2732 forms openings 2736 that are each slightly larger in diameter than each retro-reflective marker sphere 102. Each blister pack 2712 is separated from two, three or four adjacent blister packs 2712 by perforations 2742 and 2744 that extend at least through pocket layer 2722 and may extend through backing layer 2724. Perforations 2742 and 2744 allow neighboring blister packs 2712 to be separated from each other by a user tearing pocket layer 2722 and backing layer 2724 along perforation 2742. Perforations 2742 and 2744 are oriented in respective perpendicular directions shown by double-headed arrows 2752 and 2754, respectively.

In one embodiment of the present invention, a blister strip or blister card may be produced by vacuum-forming or thermo-forming the "pockets." Compression plates or rollers may be used to apply the backing heaters that adhere the backing substrates to the pocket layer.

Although FIG. 27 shows a blister card used with one particular type of retro-reflective marker sphere, the blister cards of the present invention may be used with various types of retro-reflective marker spheres, including retro-reflective marker spheres for both threaded and snap-on posts.

In some embodiments of the present invention, blister packs similar to blister packs 2302 and 2502 may be arranged in a two-dimensional blister card similar to blister card 2702. Also, a blister card of the present invention may have any number of blister packs in any two-dimensional arrangement.

In one embodiment of the present invention, the pocket layer of each blister pack is made of a transparent or translucent plastic, and the backing layer may be made of materials such as plastic, paper, cloth, metal foil, a combination of materials, etc., to which the pocket layer is adhered using an adhesive that allows the pocket layer to be removed from the backing layer, thereby allowing a retro-reflective marker sphere to be removed from the blister pack by a user.

In one embodiment of the present invention, the pocket layer of each blister pack is made of a transparent or translucent plastic, and the backing layer is made of a rupturable material, such as metal foil, similar to the blister packs used with pills and tablets. The backing layer may be joined to the pocket layer using an adhesive, by thermoforming the backing layer to the pocket layer, or by any other process for joining the backing layer of a blister pack to the pocket layer of a blister pack. Such a configuration allows a retro-reflective marker sphere to be removed from a blister pack by pressing down on the dome-shaped pocket of the blister pack, thereby forcing the retro-reflective marker sphere through the opening in the pocket layer and rupturing the rupturable material of the backing layer.

Although the blister packs shown in the drawings are shown as being used with a particular retro-reflective marker sphere of the present invention, the blister packs of the present invention may be used with various types of retro-reflective marker spheres, such as the snap-on retro-reflective spheres shown in FIGS. 10, 28, 29, 30, 31, 32, 33, 34, 35 and 36, as well as with other types of retro-reflective marker spheres.

FIGS. 28, 29, 30 and 31 show a retro-reflective marker sphere 2802 according to one embodiment of the present invention. Retro-reflective marker sphere 2802 is a snap-on retro-reflective marker sphere that is designed to snap onto a snap-on mounting post of a medical device (not shown in FIGS. 28, 29, 30 and 31). Retro-reflective marker sphere 2802 comprises a core ball 2812 on which is mounted an upper retro-reflective covering piece 2814 and a lower retro-reflective covering piece 2816. Upper retro-reflective covering piece 2814 and lower retro-reflective covering piece 2816 are generally hemispherical in shape. Where upper retro-reflective covering piece 2814 and lower retro-reflective covering piece 2816 meet there is a seam 2818. Lower retro-reflective covering piece 2816 includes a circular opening 2820. Core ball 2812, shown in detail in FIGS. 32, 33, 34, 35 and 36, has a generally spherical body portion 2832, a mounting recess 2834, an upper central circular (dimple) divet 2838 and sixteen upper peripheral circular (dimples) divets 2840. Mounting recess 2834 is circular in cross-section and has a circular opening 2844. In the embodiment shown, upper retro-reflective covering piece 2814 covers an upper half 2872 of core ball 2812, and lower retro-reflective covering piece 2816 covers a lower half 2874 of core ball 2812. Retro-reflective marker sphere 2802 and core ball 2812 have an axis shown by double-headed dashed arrow 2890, shown in FIG. 28, that extends through the center of mounting recess 2834. Together, upper retro-reflective covering piece 2814 and lower retro-reflective covering piece 2816 form a retro-reflective covering 2892 that is generally spherical in shape.

Figure 35:
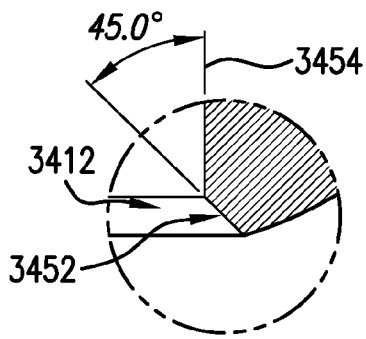
FIG. 35 is a close-up view of one of the two dashed-circled regions of FIG. 34.
Figure 36:
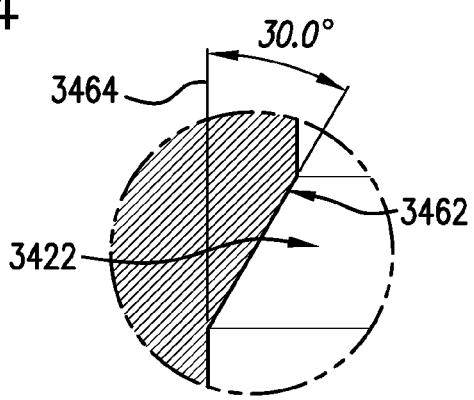
FIG. 36 is a close-up view of the other dashed-circled region of FIG. 34.

FIGS. 32, 33, 34, 35 and 36 show core ball 2812 and details of mounting recess 2834. Mounting recess 2834 includes a flared recess base portion 3412, a cylindrical recess lower portion 3414, a cylindrical recess waist portion 3416, a recess chamfered portion 3418, a cylindrical recess middle portion 3420, a recess frustoconical portion 3422, a cylindrical recess upper portion 3424 and a recess top 3426. Because recess waist portion 3416 is smaller in diameter than recess lower portion 3414, a ledge 3432 is formed at an upper end 3434 of recess lower portion 3414. Recess waist portion 3416 has a cylindrical wall 3436. Details of dashed-circled regions 3442 and 3444 are shown in FIGS. 35 and 36, respectively. Although as shown in FIG. 35 the angle of an angled wall 3452 of recess base portion 3412 with respect to a line 3454 parallel to the axis of core ball 2812 is 45°, this angle may vary depending on the particular mounting post on which retro-reflective marker sphere 2802 is to be mounted. Similarly, although as shown in FIG. 36 the angle of an angled wall 3462 of recess frustoconical portion 3422 with respect to a line 3464 parallel to the axis of core ball 2812 is 30°, this angle may vary depending on the particular mounting post on which retro-reflective marker sphere 2802 is to be mounted. Together, ledge 3432, cylindrical wall 3436 and angled wall 3452 define a raised rim 3472 that projects into mounting recess 2834.

Figure 37:
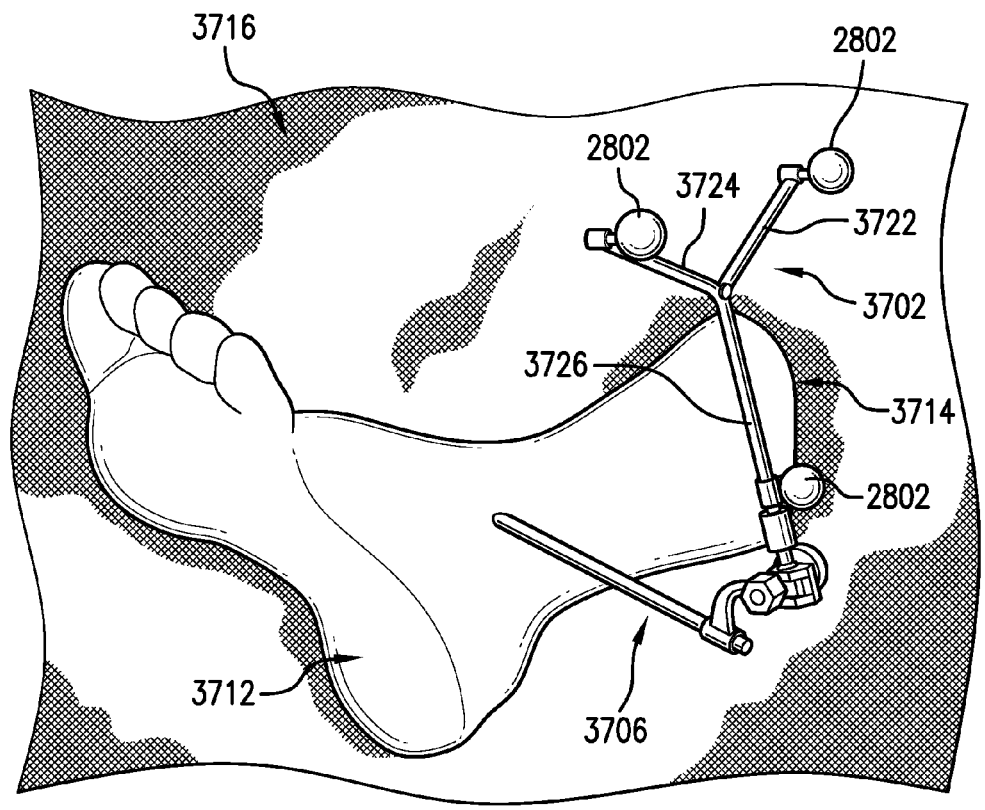
FIG. 37 is a perspective view of a medical device, mounted on a human foot, on which are mounted retro-reflective marker spheres according to one embodiment of the present invention.

FIG. 37 shows a medical device 3702 on which are mounted three retro-reflective marker spheres 2802. Medical device 3702 functions similarly to medical device 702. Medical device 3702 is mounted by a mounting device 3706 on a human foot 3712 extending through an opening 3714 in a covering blanket 3716. Medical device 3702 includes three arms 3722, 3724 and 3726.

Figure 38:
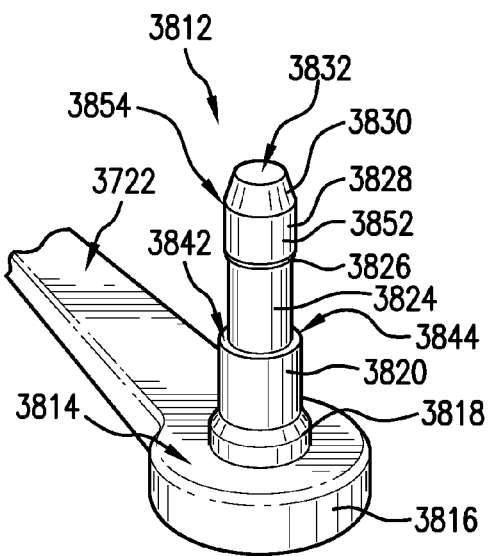
FIG. 38 is a perspective view of a snap-on mounting post on an arm of the medical device of FIG. 37.

FIG. 38 shows a snap-on mounting post 3812 that is mounted on an upper surface 3814 of a circular end 3816 of arm 3722 of medical device 3702. Mounting post 3812 includes a post base 3818, a cylindrical post lower portion 3820, a cylindrical post middle portion 3824, a post upper chamfered portion 3826, a cylindrical post upper portion 3828, a post frustoconical portion 3830 and a post top 3832. Post lower portion 3820 includes an upper surface 3842 having a circular peripheral edge 3844. Together post upper chamfered portion 3826, post upper portion 3828, post frustoconical portion 3830 and post top 3832 are part of a post upper end 3852 having a post upper end surface 3854.

Figure 39:
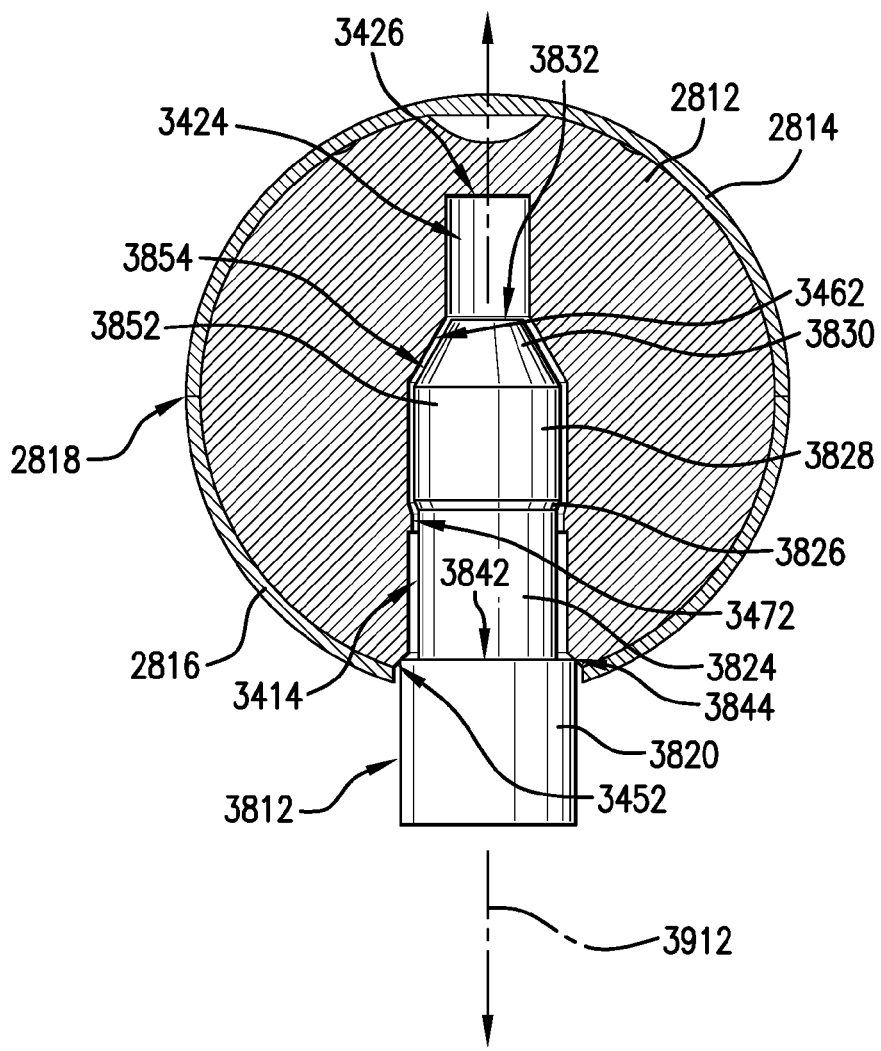
FIG. 39 is a cross-sectional view of the retro-reflective marker sphere of FIG. 1 mounted on the snap-on mounting post of FIG. 38.

FIG. 39 shows retro-reflective marker sphere 2802 snapped onto snap-on mounting post 3812 by forcing retro-reflective marker sphere 2802 onto snap-on mounting post 3812. Because core ball 2812 is made of a resilient material, mounting recess 2834 is able to spread open slightly so that raised rim 3472 can slide along post upper end surface 3854 as retro-reflective marker sphere 2802 is forced onto snap-on mounting post 3812. Raised rim 3472 eventually reaches post middle portion 3824 and snaps into place beneath post upper end 3852. Retro-reflective marker sphere 2802 is held in place on snap-on mounting post 3812 by post upper end 3852 being trapped between recess frustoconical portion 3422 and raised rim 3472. angled wall 3452 of recess base portion 3412 abuts circular peripheral edge 3844 upper surface 3842 of post lower portion 3820. Snap-on mounting post 3812 has an axis 3912.

In some embodiments of the present invention, a blister pack of the present invention may include two or more backing layers. For example, one backing layer may be made of a stiff or semi-stiff material such as cardboard or a stiff plastic that provides structural stability to the blister pack. In such an embodiment, the backing layer made of the stiff or semi-stiff material may include openings that are aligned with and in communication with openings of the pockets of the pocket layer. Each opening in the backing layer may have the same shape as the opening at the bottom of the respective pocket with which the opening of the backing layer is aligned. The openings in the backing layer also may be roughly the same diameter as the openings of the pockets or may be larger than the openings of the pockets. The two backing layers may be joined to each other by various means, such as an adhesive, and the backing layer made of the stiffer material is in turn joined to the pocket layer.

Figure 40:
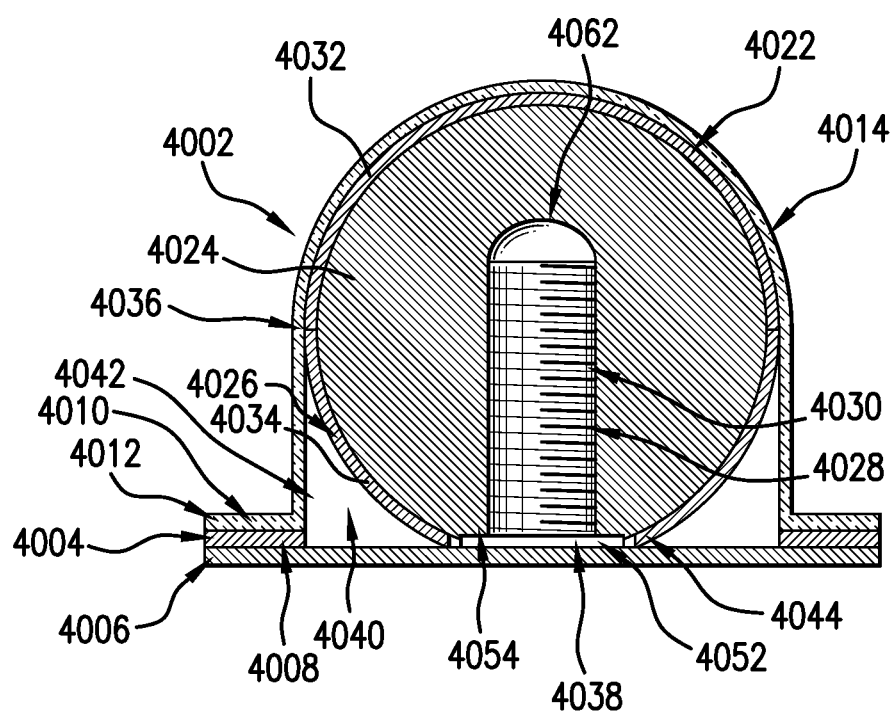
FIG. 40 is a cross-sectional view of a packaged retro-reflective marker sphere according to one embodiment of the present invention.

FIG. 40 shows an example of a blister pack 4002 according to one embodiment of the present invention having two backing layers, i.e., upper backing layer 4004 and lower backing layer 4006. Lower backing layer 4006 is joined to a lower surface 4008 of upper backing layer 4004. Joined to an upper surface 4010 of upper backing layer 4004 is a pocket layer 4012 having a dome-shaped pocket 4014. Upper backing layer 4004 may be made of a stiff or semi-stiff material such as cardboard or a stiff plastic that provides structural stability to blister pack 4002. Lower backing layer 4006 may be made of a rupturable or a non-rupturable material. FIG. 40 shows a retro-reflective marker sphere 4022 in blister pack 4002. Retro-reflective marker sphere 4022 includes a generally spherical core ball 4024 to which is adhered a generally spherical retro-reflective covering 4026. Core ball 4024 includes a mounting recess 4028 having an interior screw thread 4030. Retro-reflective covering 4026 is comprised of a generally hemispherical upper retro-reflective covering piece 4032 and a generally spherical lower retro-reflective covering piece 4034 that meet at a seam 4036. Lower retro-reflective covering piece 4034 includes a circular opening 4038. Upper backing layer 4004 includes an opening 4040 that is aligned and in communication with an opening 4042 of pocket 4014. A lower edge 4044 of lower retro-reflective covering piece 4034 abuts lower backing layer 4006. There is a gap 4052 between a base 4054 of core ball 4024 and lower backing layer 4006. Mounting recess has a distal end 4062.

If lower backing layer 4006 is made of a rupturable material, retro-reflective marker sphere 4022 may be removed from blister pack 4002 by a user pressing down on pocket 4014, to thereby forcing retro-reflective marker sphere 4022 through opening 4042 in upper backing layer 4004 and thereby rupturing the rupturable material of lower backing layer 4006.

If lower backing layer 4006 is made of a non-rupturable material, pocket layer 4012 may be adhered to upper surface 4010 of upper backing layer 4004 by an adhesive that allows pocket layer 4012 to be manually removed from upper backing layer 4004 to thereby open blister pack 4002.

A series of blister packs 4002 may be part of a blister strip similar to blister strip 2102. Blister packs 4002 may also be part of a blister card similar to blister card 2702.

Although only one type of blister pack employing two backing layers is shown in FIG. 40, various types of blister packs may be made using two layers according to various embodiments of the present invention. For example, a rupturable layer of a two-backing layer blister pack may include a recess for a mounting base such as that shown in FIGS. 23 and 24 or an opening for a mounting base such as that shown in FIGS. 25 and 26.

Although one type of retro-reflective marker sphere is shown packaged in the blister pack shown in FIG. 40, a blister pack with two backing layers may be used with various types of retro-reflective marker spheres.

Although only two backing layers are shown in FIG. 40, a multiple-backing-layer blister pack of the present invention may have three or more backing layers.

Figure 41:
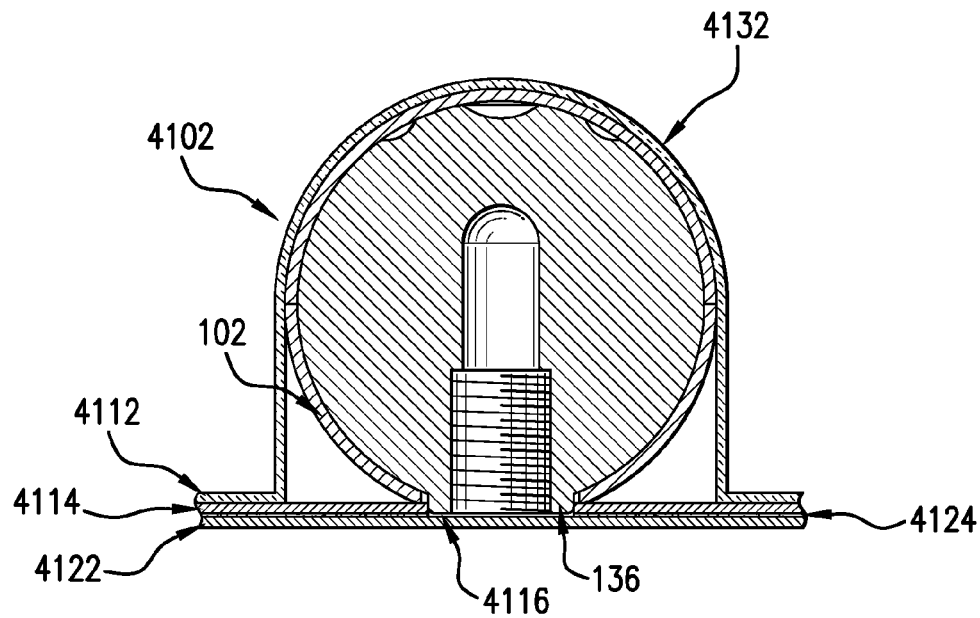
FIG. 41 is a cross-sectional view of a packaged retro-reflective marker sphere according to one embodiment of the present invention.
Figure 42:
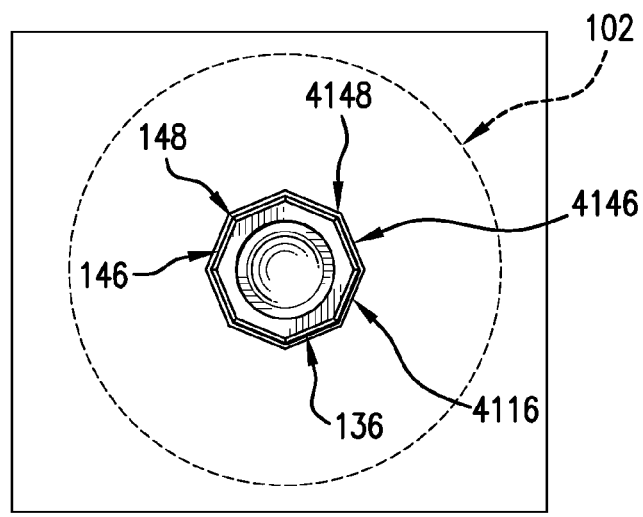
FIG. 42 is a bottom plan view of the packaged retro-reflective marker sphere of FIG. 41.

FIGS. 41 and 42 show a retro-reflective marker sphere 102 in a blister pack 4102 according to one embodiment of the present invention comprising a transparent or translucent pocket layer 4112 and a backing layer 4114 joined to pocket layer 4112. Backing layer 4114 includes a octagonal-shaped opening 4116. Mounting base 136 extends through circular-shaped opening 4116 to thereby help keep retro-reflective marker sphere 102 in right-side-up orientation in blister pack 4102. FIG. 41 shows a protective layer 4122 that is joined to backing layer 4114 to protect mounting base 136. Protective layer 4122 is joined to backing layer 4114 using an adhesive 4124. Adhesive 4124 may not be present in the region beneath mounting base 136 to avoid adhesive 4124 possibly sticking to mounting base 136. Adhesive 4124 on protective layer 4122 is sufficiently weak to allow protective layer 4122 to be removed from backing layer 4114. Once protective layer 4122 is removed from backing layer 4114, retro-reflective marker sphere 102 may be screwed onto a mounting post, such as mounting post 812 (not shown in FIGS. 41 and 42), while still in blister pack 4102. Retro-reflective marker sphere 102 may then be removed from blister pack 4102. Pocket layer 4112 includes a dome-shaped pocket 4132 that contains retro-reflective marker sphere 102. A series of blister packs 4102 may be part of a blister strip similar to blister strip 2102. Octagonal-shaped opening 4116 includes eight sides 4146 and eight corners 4148.

In one embodiment of the present invention, a user may screw retro-reflective marker sphere 102 onto a mounting post by grasping retro-reflective marker sphere 102 through pocket 4132 and turning retro-reflective marker sphere 102 on the thread of the mounting post. In this case sides 4146 and corners 4148 of octagonal-shaped opening 4116 engage respective sides 146 and corners 148 of mounting base 136 to aid in turning retro-reflective marker sphere 102.

In one embodiment of the present invention, a user may screw retro-reflective marker sphere 102 onto a mounting post by grasping pocket 4132 and turning pocket 4132 to cause sides 4146 and corners 4148 of octagonal-shaped opening 4116 to engage respective sides 146 and corners 148 of mounting base 136 thereby turn retro-reflective marker sphere 102 and screw retro-reflective marker sphere 102 onto the mounting post.

In one embodiment of the present invention, the core ball of a retro-reflective marker sphere of the present invention may be made of an injection-moldable plastic such as a thermoplastic polyester elastomer. Other types of materials that may be used to form the core ball include polyethylene, polypropylene and other thermoplastic elastomers.

Figure 43:
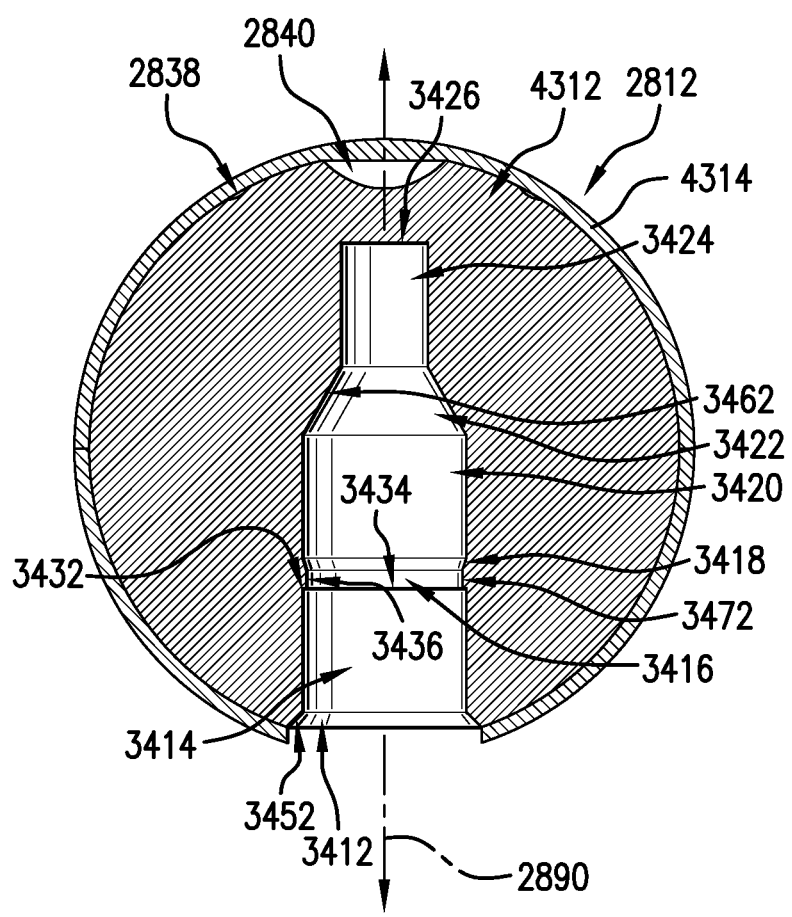
FIG. 43 is a cross-sectional view of the core ball of FIG. 32 taken along line B-B of FIG. 33 according to an alternate embodiment.

FIG. 43 shows core ball 2812 and details of mounting recess 2834. Mounting recess 2834 includes a flared recess base portion 3412, a cylindrical recess lower portion 3414, a cylindrical recess waist portion 3416, a recess chamfered portion 3418, a cylindrical recess middle portion 3420, a recess frustoconical portion 3422, a cylindrical recess upper portion 3424 and a recess top 3426. Because recess waist portion 3416 is smaller in diameter than recess lower portion 3414, a ledge 3432 is formed at an upper end 3434 of recess lower portion 3414. Recess waist portion 3416 has a cylindrical wall 3436. Although the angle of an angled wall 3452 of recess base portion 3412 with respect to a axis 2890 of core ball 2812 is 45°, this angle may vary depending on the particular mounting post on which retro-reflective marker sphere 2802 is to be mounted. Together, ledge 3432, cylindrical wall 3436 and angled wall 3452 define a raised rim 3472 that projects into mounting recess 2834.

The material 4312 of core ball 2812 may comprise a filler material such as an MRI filling material. The MRI filling material is capable of being registered on machine equipment utilized in an MRI exam or procedure. Utilizing MRI filling material eliminates additional manufacturing processes and materials for constructing retro-reflective surfaces on the outside of core ball 2812. Disclosed embodiments of the MRI filling material may comprise water, watery liquids, gel or fat. In some disclosed embodiments, the viscosity ranges of the MRI filling material may range between approximately 1 cP (Centipoise) or cSt (Centistokes) to 1840 cp or cSt. Material 4312 is contained within core ball 2812. In one disclosed embodiment, material 4312 is encapsulated within a cavity of core ball 2812 between mounting recess 2834 and a covering layer 4314. An access hole may be created in upper peripheral circular (dimple) divet 2840, but below covering layer 4314, to introduce material 4312 within the cavity of core ball 2812. Once the cavity of core ball 2812 is filled with the filler material, the access hole may be plugged to prevent leakage therefrom. Because the access hole is disposed in upper peripheral circular (dimple) divet 2840 and below covering layer 4314, no interference occurs at covering layer 4314. This feature reduces additional manufacturing steps for generating the disclosed design in an efficient and functional manner. Thus, in some embodiments, MRI filling material, such as water, watery liquids, gel or fat, may be injected within the cavity of core ball 2812 to provide a filler material.

In some embodiments of the present invention the retro-reflective covering of a retro-reflective marker sphere may be a two-piece retro-reflective covering, as shown in FIGS. 1, 2, 3, 4, 5, 6, 10, 28, 29, 30, 31, 32, 33, 34, 35 and 36. However, in other embodiments of the present invention, the retro-reflective covering may be made as a single piece. In one embodiment of the present invention, the upper and lower retro-reflective coverings may each be formed by thermoforming a piece of retro-reflective material to the appropriate trimming of the material before and/or after thermoforming. Such thermoforming allows the thickness of the retro-reflective covering to be controlled to a constant thickness throughout the retro-reflective covering.

In one embodiment of the present invention, such as shown in FIGS. 1, 2, 3, 4, 5, 6, 10, 28, 29, 30, 31, 32, 33, 34, 35 and 36, there is no or virtually no gap at the seam between the upper and lower retro-reflective covering pieces. In one embodiment, the gap may be minimized or eliminated by controlling the dimensions of the formed and cut hemispheres and designing the upper and lower retro-reflective covering pieces so that the open end of each of the upper and lower retro-reflective covering pieces butt up to each other during automated assembly. The upper and lower retro-reflective covering piece may be adhered to the core ball by applying a UV-curable adhesive via syringe tip, blade, spray or brush to the core ball and then curing the bond through the upper and lowering covering pieces with a combination of light and/or UV-ray intensity and time. Similar procedures may also be employed to eliminate or reduce the gaps in retro-reflective coverings comprising three or more pieces.

In one thermoforming process that may be used to form the upper and lower retro-reflective coverings, a starting material is chosen that is constant in thickness. A vacuum forming is used that allows an entire sheet of the retro-reflective covering material to be heated, stretched and then vacuum-formed into multiple identical-shaped nests to form exact replicas of each other. The heating, stretching and vacuum application steps of the process may be controlled to provide consistency from cycle to cycle (each forming multiple hemispherical coverings). The consistent manner in which the material is heated and stretched, and the equal application of the vacuum across the surface of each section of covering to be formed, creates a consistent thickness across the entire hemisphere of the retro-reflective covering.

In one embodiment of the present invention, the thickness of the retro-reflective covering may vary by no more than 0.003" (0.00762 cm) throughout the retro-reflective covering. Suitable retro-reflective materials include 3M 8350 Scotchlite reflective pressure sensitive adhesive (PSA) films (made by 3M). In one embodiment of the present invention, the retro-reflective coating may be a layer of a retro-reflective paint.

The upper and lower retro-reflective coverings may be mounted on the core ball using an adhesive. Suitable adhesives include cyanoacrylates, light-cure adhesives, UV-cure adhesives, etc. When a UV-cure adhesive is used, the adhesive may be cured by exposing the covered core ball to UV light to adhere the upper and lower retro-reflective coverings to the core ball.

Although in some embodiments of the present invention shown in FIGS. 1, 2, 3, 4, 5, 6, 10, 28, 29, 30, 31, 32, 33, 34, 35 and 36 the core ball has eight smaller circular peripheral divets surrounding one larger central circular divet, the core ball may have various numbers, sizes and shapes of divets, and the divets may be arranged in various patterns. One purpose of the central divet is to provide a recess at the location of the gate for the injection mold cavity for the core ball. Because the gate for the cavity for the core ball is located in a recessed region, i.e., the central divet, when the core ball is removed from the runner after molding, it is not necessary to sand down any remaining plastic material at the gate. The number and/or arrangement of peripheral divets on a core ball may be used to identify the cavity of a mold in which a particular core ball is formed. For example, eight peripheral divets may indicate one cavity in a mold, seven peripheral divets may identify a second cavity of a mold, etc. When multiple molds are used to form core balls, the number and/or arrangement of peripheral divets may identify a particular cavity of a particular mold. Also, although in the embodiments of the present invention shown in FIGS. 1, 2, 3, 4, 5, 6, 10, 28, 29, 30, 31, 32, 33, 34, 35 and 36 the core ball includes divets, in other embodiments of the present invention, the core ball may not include either a central divet and/or peripheral divets. In a core ball that does not include a central divet, the surface of the core ball may be sanded or otherwise smoothed to remove plastic material remaining at the gate for the core ball after the core ball has been removed from a runner after injection molding.

In one embodiment of the present invention, the core ball of a retro-reflective marker sphere may be radiopaque for use in CT scanning (computed tomography scanning). In some embodiments of the present invention, the retro-reflective marker may be suitable for using in magnetic resonance imaging (MRI).

In one embodiment of the present invention, the core ball may have a radiopaque loading of >12%, i.e., the core ball is greater than 12% radiopaque. In one embodiment of the present invention, the core ball may be made radiopaque by loading barium into the resin for the core ball prior to injection molding of the core ball. In one embodiment of the present invention, the mounting recess of the core ball may be designed to allow the retro-reflective marker sphere to be snapped onto a mounting post.

Although in some embodiments of the present invention, the retro-reflective covering and covering pieces of the retro-reflective marker sphere may be gray and/or silver in color, in other embodiments of the present invention, the retro-reflective coverings and covering pieces may be gold, white or chrome in color to provide better reflectivity than retro-reflective coverings and covering pieces that are gray and/or silver in color. Examples of materials that may be used for gold, white and chrome retro-reflective coverings include glass beads, reflective inks, reflective paints and reflective tapes.

In one embodiment of the present invention, the upper half and the lower half of the core ball may have different colors to aid in determining if the upper retro-reflective covering and the lower retro-reflective covering are mounted properly on the core ball. If the upper retro-reflective covering or the lower retro-reflective covering is not mounted properly on the core ball, the upper or lower half of the core ball, respectively, will be visible. Based on the color visible, a user will be able to determine if the upper retro-reflective covering piece or the lower retro-reflective covering piece is not mounted properly on the core ball.

In one embodiment of the present invention, the retro-reflective marker spheres may be compatible with Brainlab™ navigation systems. In one embodiment of the present invention, retro-reflective marker spheres are visible using x-ray and CT imaging. The retro-reflective marker spheres may provide auto-registration and localization of anatomical structures that enable surgeons to wirelessly track the position and orientation of any device from a frame of reference.

In one embodiment of the present invention, the retro-reflective marker sphere may be made in one, two or more pieces of a retro-reflective material. For example, a transparent plastic filled with retro-reflective filler material, such as solid or hollow microspheres, may be used to form an injection molded retro-reflective marker sphere in or two pieces. If the retro-reflective microsphere is molded in two pieces, the two pieces may be joined using an adhesive and/or mating engagement structures on the two pieces. For example, one piece may be screwed into the other piece, the two pieces may have one or more combinations of tab recesses and mating tabs, the two pieces may have one or more combinations of pin recesses and mating pins, etc. Examples of filler materials for the transparent plastic to make the plastic retro-reflective include Scotchlite® glass microspheres made by 3M.

Having described the many embodiments of the present invention in detail, it will be apparent that modifications and variations are possible without departing from the scope of the present invention defined in the appended claims. Furthermore, it should be appreciated that all examples in the present disclosure, while illustrating many embodiments of the present invention, are provided as non-limiting examples and are, therefore, not to be taken as limiting the various aspects so illustrated.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof.

What is claimed is:

1. A device comprising a retro-reflective marker sphere comprising:
   a core ball comprising:
      a generally spherical body portion, and
      a mounting recess extending into the body portion of the core ball, and
   a retro-reflective covering on the core ball,
   wherein the retro-reflective covering has an opening aligned with the mounting recess of the core ball,
   wherein the mounting recess includes one or more interior engagement structures for engaging one or more exterior engagement structures of a mounting post when the retro-reflective marker sphere is mounted on a mounting post, and
   wherein the core ball comprises an MRI filling material contained in the core ball.

2. The device of claim 1, wherein the MRI filling material is encapsulated in the core ball.

3. The device of claim 1, wherein the MRI filling material comprises a gel.

4. The device of claim 1, wherein the MRI filling material comprises a fat.

5. The device of claim 1, wherein the MRI filling material comprises water.

6. The device of claim 1, wherein the MRI filling material has a viscosity range of from approximately 1cP to 1840 cp.

7. The device of claim 1, wherein the mounting recess includes one or more interior snap-on engagement structures for engaging one or more exterior snap-on engagement structures of the mounting post when the retro-reflective marker sphere is mounted on the mounting post.

8. The device of claim 1, wherein the retro-reflective covering comprises only two pieces and wherein the opening in the retro-reflective covering is in only one of the two pieces.

* * * * *